US008670993B2

(12) United States Patent
Henley

(10) Patent No.: US 8,670,993 B2
(45) Date of Patent: Mar. 11, 2014

(54) METHOD AND SYSTEM FOR PROVIDING AN ON-LINE HEALTHCARE OPEN MARKET EXCHANGE

(75) Inventor: Julian Henley, New Haven, CT (US)

(73) Assignee: PriceDoc, Inc., Solana Beach, CA (US)

( * ) Notice: Subject to any disclaimer, the term of this patent is extended or adjusted under 35 U.S.C. 154(b) by 550 days.

(21) Appl. No.: 12/898,936

(22) Filed: Oct. 6, 2010

(65) Prior Publication Data

US 2011/0022479 A1 Jan. 27, 2011

Related U.S. Application Data

(60) Continuation-in-part of application No. 12/461,708, filed on Aug. 21, 2009, now abandoned, which is a division of application No. 09/725,142, filed on Nov. 29, 2000, now Pat. No. 7,657,479.

(60) Provisional application No. 60/222,648, filed on Aug. 3, 2000, provisional application No. 60/201,021, filed on May 1, 2000, provisional application No. 60/186,542, filed on Mar. 2, 2000.

(51) Int. Cl.
*G06Q 10/00* (2012.01)
*G06Q 50/00* (2012.01)

(52) U.S. Cl.
USPC .................................................. 705/2; 705/3

(58) Field of Classification Search
None
See application file for complete search history.

(56) References Cited

U.S. PATENT DOCUMENTS

| 5,794,219 | A | 8/1998 | Brown |
| 5,918,208 | A | 6/1999 | Javitt |
| 5,964,700 | A | 10/1999 | Tallman et al. |
| 5,995,939 | A | 11/1999 | Berman et al. |
| 6,006,191 | A * | 12/1999 | DiRienzo ........................... 705/2 |
| 6,014,629 | A | 1/2000 | DeBruin-Ashton |
| 6,035,276 | A | 3/2000 | Newman et al. |

(Continued)

OTHER PUBLICATIONS

Lorraine Santoli, "Bid for Surgery, Web Site Auction Empower Healthcare Consumers" Medicine Online Public Relations, 1999, (2 pages).

*Primary Examiner* — Michelle L Le
(74) *Attorney, Agent, or Firm* — Nixon & Vanderhye, P.C.

(57) ABSTRACT

An Internet-based competitive pricing and bidding transaction system includes one or more transaction processing servers that interface and communicate over the Internet with client computer systems of prospective online consumers, medical and professional/licensed services providers and a plurality of related information databases. The transaction processing system handles online communications and procedures for conducting auctions for delivery of proffered medical and professional/licensed services and maintains a registration database of service providers and online prospective consumers/bidders. Medical and professional/licensed services providers may include licensed doctors/nurses, licensed veterinary doctors/technicians as well as conventional homecare/hospice providers, physical therapy providers, babysitting and other professional caretaker services that can provided to/for man or animal. The online proffered services may include conventional medical treatment and/or veterinary services provided for animals, pets or other creatures. A professional license authentication/qualifier engine is provided which transparently and automatically researches, verifies and updates professional credentials, accreditations and background information of each professional service provider upon registration of that service provider with the transaction system, and makes that information available to prospective registered bidders online.

5 Claims, 17 Drawing Sheets

NON-LIMITING EXAMPLE HEALTH MARKET EXCHANGE TRANSACTION SYSTEM

(56) References Cited

U.S. PATENT DOCUMENTS

| | | |
|---|---|---|
| 6,035,288 A | 3/2000 | Solomon |
| 6,151,581 A | 11/2000 | Kraftson et al. |
| 6,167,386 A | 12/2000 | Brown |
| 6,289,319 B1 | 9/2001 | Lockwood |
| 6,366,891 B1 | 4/2002 | Feinberg |
| 6,415,270 B1 | 7/2002 | Rackson et al. |
| 6,415,320 B1 | 7/2002 | Hess et al. |
| 6,466,917 B1 | 10/2002 | Goyal et al. |
| 6,606,607 B1 | 8/2003 | Martin et al. |
| 6,665,649 B1 | 12/2003 | Megiddo |
| 6,671,674 B1 | 12/2003 | Anderson et al. |
| 6,704,713 B1 | 3/2004 | Brett |
| 6,732,161 B1 | 5/2004 | Hess et al. |
| 6,847,939 B1 | 1/2005 | Shemesh |
| 6,856,963 B1 | 2/2005 | Hurwitz |
| 2002/0013774 A1 | 1/2002 | Morimoto |
| 2002/0128879 A1* | 9/2002 | Spears .................. 705/4 |
| 2004/0260577 A1 | 12/2004 | Dahlin et al. |
| 2004/0267579 A1 | 12/2004 | Markman |
| 2006/0136264 A1 | 6/2006 | Eaton et al. |
| 2008/0167998 A1 | 7/2008 | Hyte |

\* cited by examiner

NON-LIMITING EXAMPLE HEALTH MARKET EXCHANGE TRANSACTION SYSTEM

NON-LIMITING EXAMPLE
TRANSACTION SYSTEM OVERVIEW DIAGRAM

NON-LIMITING EXAMPLE
HME WEB-SITE PAGE LINKS

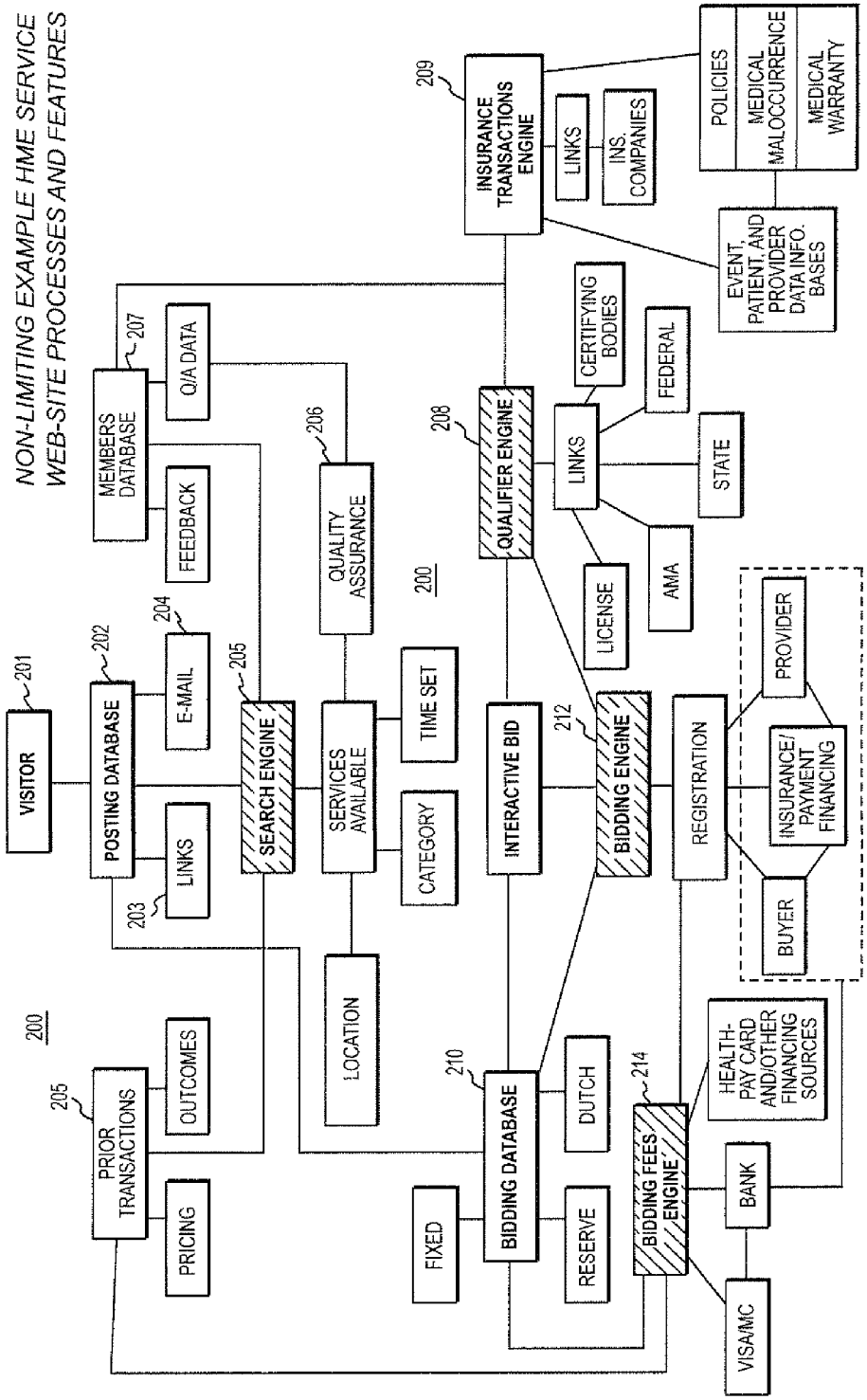

NON-LIMITING EXAMPLE USER RESOURCES

NON-LIMITING EXAMPLE BIDDER PAYMENT OPTIONS

NON-LIMITING EXAMPLE ACCOUNT PROFILE AND SIGN UP PROCESS:

NON-LIMITING EXAMPLE PAYMENT PROCESS

NON-LIMITING EXAMPLE FINANCING PROCESS AND OPTIONS

METHOD AND SYSTEM FOR PROVIDING AN ON-LINE HEALTHCARE OPEN MARKET EXCHANGE

RELATED APPLICATIONS

This application is a continuation-in-part, which claims the benefit of the following U.S. Provisional Applications, the entire content of each of which is hereby incorporated by reference into this application:

(1) "Method and System for the Provision of Medical Services" to Julian L. Henley, Ser. No. 60/186,542, filed Mar. 2, 2000;

(2) "Method and Apparatus for the Provision of Medical Services" to Julian L. Henley, Ser. No. 60/201,021, filed May 1, 2000; and (3) "Medical Transaction Overview" to Julian L. Henley, Ser. No. 60/222,648, filed Aug. 3, 2000.

This continuation-in-part application also claims the benefit of parent U.S. application Ser. No. 12/461,708, filed Aug. 21, 2009, which is a divisional of U.S. application Ser. No. 09/725,142, filed Nov. 29, 2000, now U.S. Pat. No. 7,657,479, the entire content of each of which is hereby incorporated by reference into this application.

FIELD

The exemplary non-limiting illustrative embodiments disclosed herein relate to a method and system for implementing an on-line healthcare market exchange via the Internet to serve as an "one stop" full service marketplace for doctors, patients, and other medical/healthcare service providers including professional veterinary and animal healthcare/medical services. More particularly, the non-limiting example embodiments disclosed herein relate to a method and system for implementing an on-line transaction system that reduces transactional costs associated with providing and acquiring professional services by providing a web-site that provides consumers with comparative pricing information and enables or facilitates open negotiating over the Internet between consumers and providers for all types of professional medical/healthcare services including veterinary and animal healthcare services.

BACKGROUND AND SUMMARY

During the advent of a booming e-commerce over the Internet, many people have become familiar with the flexibility and cost effectiveness of shopping "on line" for various goods via the use of Internet sites that offer public auctioning forums of one sort or another where sellers and buyers may participate in some form of interactive bidding process. However, while on-line auctioning has been employed somewhat successfully in the context of bartering for various products, problems arise when trying to accommodate the need for assessing professional service provider qualifications, scheduling, location and quality. One of the problems confronting a consumer willing to bid on-line for professional services is that there is not any convenient means for verifying the qualifications or for assessing the quality of services likely to be rendered by a prospective unknown service provider who puts up his/her services for auction. Moreover, it would be highly desirable for someone in need of medical services to be able to have access on-line to a convenient "one stop" full service market place that can provide access to health care payment plans, various financing options and even related insurance products. For example, most medical care consumers would find it very helpful to have access to an Internet web-site or service that offers an on-line medical services information repository or provides a convenient and comprehensive way for researching the reputation and quality of various healthcare service providers. It also would be very convenient and useful for on-line consumers to have the ability to access a single main Internet web-site or home page that provides Internet links and/or on-line tools that automatically perform or at least assist in arranging financing and making payment arrangements for procured medical/healthcare services. Furthermore, it would be very convenient and useful for an on-line consumer to have the ability to search and access related services such as medical insurance coverage for procured services through the same main Internet web-site.

On-line auction systems are known to have been attempted only for a few types of professional services. For example, U.S. Pat. No. 6,006,191 to DiRienzo (1999) discloses a system wherein certain limited medical services of remote physicians' are auctioned, to wit, DiRienzo is specifically directed toward the reading of radiological and other medical images (i.e., image-reading diagnostic services). In this context, DiRienzo generally teaches:

"... The essence of the invention is the use of a decentralized, i.e., self-organizing, distribution system combined with bid queues to establish a market place which allows for continuously negotiated prices with control (over who reads the images, when they are read and what the fee will be for such a reading) being totally in the hands of the patient/gate keeper and the diagnostic physician." [column 8, lines 31-37].

Additional prior art patents of possible interest include:
U.S. Pat. No. 5,918,208—Javitt (1999)
U.S. Pat. No. 5,964,700—Tallman et al (1999)
U.S. Pat. No. 5,995,939—Berman et al (1999)
U.S. Pat. No. 6,014,629—DeBruin-Ashton (2000)
U.S. Pat. No. 6,035,288—Solomon (2000)
U.S. Pat. No. 6,289,319—Lockwood (2001)

Javitt is directed to a system that allows a doctor to forecast utilization of services. Tallman et al discloses an on-line system that allows an insurance company member to select the most appropriate doctor. Berman et al teaches an e-mail system between doctors and others involved in a specific patient's health care. DeBruin-Ashton teaches a method of compiling a customized directory of medical service providers for a particular patient. Solomon is generally directed to on-line bidding for a service (i.e., any service, medical or otherwise) in which the price can be negotiated. Lockwood discloses an automated business and financial transaction system terminal for filing and processing loan applications and the like with a financial or banking institutions to make their services available at all hours from one or more remote locations.

More recently, a company called HealthMarkets, Inc. is purportedly providing an on-line resource for locating and comparing prices of proffered health care services/physicians for the purpose of selling insured Consumer Driven Health Plans. (This company currently maintains an Internet web-site having a uniform resource locator (URL) address of "HealthMarkets.com"). However, the company does not contract directly with health service providers nor does its web-site allow on-line customers to do so. Moreover, its web-site does not provide or support on-line auctioning of professional healthcare/veterinary services or act as a one-stop marketplace for the on-line shopping of professional healthcare/veterinary services and providers.

There are also at least several well known on-line auction and reverse bidding systems such as eBay (eBay.com) and Priceline (priceline.com), but likewise, these services do not provide on-line auctioning of professional personal and/or veterinary services or serve as a on-line marketplace for conveniently researching, procuring and financing such services.

In this regard, there exists a need to provide on-line consumers with a single convenient Internet web-site source for conducting healthcare service research, participating in healthcare service auctions and fee negotiation, making healthcare payments and related financial arrangements and/or obtaining related services such as medical procedure insurance coverage.

The illustrative exemplary non-limiting implementation described herein provides a comprehensive on-line healthcare marketplace (healthcare market exchange) and web-site for obtaining healthcare services and products that is accessible via the Internet using a conventional PC with a browser and which enables an on-line visitor/user to the web-site to participate in on-line auctions and price negotiations for proffered professional services, conduct on-line research to find an appropriate healthcare service provider, arrange financing and manage payments for purchased healthcare services/products and, inter alia, review medical insurance products and procure insurance coverage for rendered healthcare services.

In addition, the exemplary non-limiting illustrative embodiment disclosed herein is contemplated to provide an online bidding site for a wide variety of healthcare providers including all physicians, Cosmetic Surgery, Dentists, Vision Specialists, Chiropractors, MediSpas, Allied Health, elective procedures and professional veterinary services, and animal healthcare and grooming services. The exemplary non-limiting illustrative embodiment disclosed herein also enables a consumer to search for and select healthcare providers via a dynamic online, competitive bidding process, where doctors offer discounted prices and actually compete for business. The exemplary non-limiting illustrative embodiment disclosed herein provides consumers with comparative pricing information for various medical, dental, vision, chiropractic, cosmetic, medispa, allied health, elective procedures, professional veterinary services, and animal healthcare and grooming services. On-line users are also able to review details about service providers' professional practice as well as their credentials. In addition to human healthcare service providers, the exemplary non-limiting illustrative embodiment disclosed herein also acts as an online marketplace for connecting consumers looking for veterinary services, animal healthcare or animal grooming services with qualified professional service providers. In addition, the exemplary non-limiting illustrative embodiment disclosed herein helps consumers to compare and negotiate pricing on professional services and procedures in a given location in the U.S. while the providers receive the benefit of generating patients/consumers who are willing to pay directly, out of pocket to the provider for their services. Some exemplary services and procedures contemplated include dental (teeth cleaning, crowns, fillings, braces, whitening, etc.), common and preventative medical procedures (physicals, mammograms, vaccines, x-rays, etc.), vision (glasses, contacts, LASIK and PRK surgery, eye exams, etc.), cosmetic (liposuction, breast enhancement, Botox, face lift, etc.), weight loss (dieticians, nutritionists, etc.), chiropractic (back and neck pain, arthritis, soreness, sports injuries, etc.), general well-being (acupuncture, hearing aids, physical therapy, massages, etc.), as well as professional veterinary services, and animal healthcare and grooming services.

Traditional transactional costs associated with providing professional services are reduced by enabling prospective clients/patients and professional service providers to competitively negotiate fees for proffered services through an interactive professional services auction transaction system implemented on-line over a publicly accessible communications network such as the Internet. A separate on-line auction transaction system, which shares database resources with the professional services auction transaction system, is also provided for implementing an arrangement for auctioning options to purchase services (i.e., a service option) at a discount (e.g., discount coupons or analogous vehicles that are applicable toward fees charged for proffered professional services). A person-to-person network marketing arrangement and method for rewarding existing member professional service providers for recruiting prospective new service provider members and training them in the use of the on-line auction transaction systems is also fostered and supported via the on-line professional services auction transaction system. Using the same arrangement, prospective users of the on-line auctions may be rewarded for usage training and recruitment of new users.

In at least one aspect, the illustrative exemplary non-limiting implementation of an on-line healthcare market exchange disclosed herein provides a professional services auction transaction system using a digital communications network server that interfaces and communicates via the Internet with client computer systems belonging to various prospective bidders and professional service providers (e.g., personal medical, financial or legal service providers) using, for example, an exchange of HTML documents and/or JAVA script applets. A transaction system server handles on-line communications and procedures for conducting public on-line auctions for the performance of proffered professional services and maintains one or more databases of information concerning registered service providers and bidders. An authentication/qualifier engine within the system automatically researches and verifies the credentials of prospective member service providers, as well as maintains background information on all registered service providers.

Databases containing a professional service provider's credentials and other information relating to their qualifications for providing a particular medical/veterinary service, as well as one or more search engines for researching and/or verifying archived qualifications/credentials of a particular service provider are made available on-line to a member/bidder via the on-line healthcare marketplace's web-page menu driven interface. An on-line user service feedback web-page and database are provided for acquiring and maintaining comments and feedback from both service providers and their patients/clients regarding the complexity and quality of services received or provided. The transaction system may also include remote client-server hardware/software facilities for providing customized database and computational services to auction bidders and professional service providers for communicating and participating in on-line bidding activities. An integrated life and health insurance product is also provided that permits trading equity in health insurance policy death benefits when bidding for health care or medical services used for the purpose of life prolongation. The illustrative exemplary non-limiting implementation of an on-line healthcare market exchange disclosed herein is described primarily in the context of providing an on-line auctioning process for the purpose of negotiating the price for the performance of a particular personal medical service by a professional medical physician on an individual patient—this is in contrast to the obtaining of an 'impersonal' professional service or opinion that is rendered remotely such as, for example, the reading of an X-ray or an MRI image. The non-limiting example illustrative on-line healthcare market exchange implementation disclosed herein, may also be used to provide the flexibility of an on-line auctioning process for soliciting discount coupons/certificates or developing a user marketing/training network and/or for marketing other professional services such as, for example, legal or financial services.

In the context of providing an on-line auction forum for professional services, it is desirable to prospective bidders to have a convenient mechanism to verify that a selected service provider is properly qualified to perform an offered service and for informing the bidder as to the likely quality of the service to be provided at a particular time, location and price. Another problem that arises within this context is that a medical service provider has no convenient way to assess the history or physical condition of a prospective patient/pet. Since the extent and cost of treating a particular patient/pet may depend upon the patient's/pet's medical history, it may be difficult for a provider to affix a specific offering price on a particular medical service or procedure. Consequently, one beneficial feature of the exemplary on-line healthcare market exchange disclosed herein is the implementation of an on-line provision for allowing prospective medical service providers to assess the physical condition and medical history of a prospective patient. In addition, the exemplary on-line healthcare market exchange implementation disclosed herein provides a fair and symmetric mechanism for accommodating errors made in the appropriateness of rendering a particular medical service or procedure without having full knowledge of a patient's pre-existing medical condition.

In the context of obtaining personal medical services on-line, people who are uninsured or only partially covered by an insurance policy are provided a more convenient mechanism for identifying and contacting a high quality, qualified medical service provider that will provide a desired medical service at the desired quality, time, location and price. Medical service providers who own or operate medical facilities for performing such services are often willing to reduce fees if it would enable them to keep the staff and resources of their facility from being underutilized. For example, during slow or inactive periods, the under utilization of facility and staff reduces profitability and thereby drives up costs for conventionally scheduled patients.

At least one aspect of the exemplary on-line healthcare market exchange system and method enables an on-line feature/tool whereby a patient, or an agent acting on a patient's behalf, or an insurance company to perform research to identify an under-utilized medical facility. This tool/feature provided by the healthcare market exchange web-site can reduce the cost of a medical service or procedure by enabling, for example, an insurance company to negotiate a lower price for the policyholder who elects to receive treatment at that underutilized facility. For example, an uninsured patient may also use the on-line healthcare market exchange to secure medical services at a favorable price by agreeing to have the desired service performed during a period of what is otherwise expected to be facility underutilization. Such underutilized medical facilities and medical service providers also may agree to lower pricing if they receive payment at time of bid closure instead of, for example, after a customary 8-12 week post-service insurance reimbursement delay.

Subject to certain restrictions, such as the availability of an otherwise under-utilized medical facility in reasonable geographic proximity to the patient, a novel type of medical insurance policy may be offered wherein the policyholder agrees to have a desired medical procedure or service performed at an otherwise underutilized facility at "market value." The cost for such a "market value" policy can be reduced because the insurer may be able to negotiate a lower price for securing a needed service on a case-by-case basis (e.g., by contracting to have a service performed at a particular time, or within a specified range of times, in an otherwise underutilized facility). Alternatively, a novel lower-cost lifetime (or shorter period) maximum benefit insurance package could be offered in such a market. For example, the premium rate for such an insurance policy could be set proportional or inversely proportional to the residual benefit in either a linear or a non-linear fashion.

Yet another alternative is that a novel insurance package be provided in which health and death benefits are combined together. In accordance with one such contemplated example insurance package arrangement, the accrued death benefit of the policy (e.g., using the standard life insurance policy model) can be used to bid for health benefit services to preserve life. The expense (e.g., finalized bid price) of the rendered medical services is taken from the policy residual death benefit and the policy holder's death benefit then becomes the remaining balance. This creates a situation of finite resources that will impose market forces on health providers where each consumer strives to get the best quality for the best price and preserve the remaining benefit for themselves and their families. The individual again is empowered to make those critical heath care decisions and impose market forces on existing providers by means of this device and method.

Another aspect of the exemplary on-line healthcare market exchange system and business method implementation described herein is to provide members and participants with links to insurance providers, as well as to provide new types of medical/health related insurance products such as medical mal-occurrence coverage and medical warranty coverage (explained below), and also to provide on-line interactive tools to simplify the process of selecting and purchasing such. It is also anticipated that such insurance products and medical services obtained through the healthcare market exchange web-site may be purchased using funds from a personal healthcare savings account or other personal finance and that the transactions be automatically performed by the on-line healthcare market exchange system.

As mentioned above, an aspect of the exemplary on-line healthcare market exchange (HME) system and business method implementation described herein is that it offers on-line, or makes available through on-line transaction, a form of "no fault" medical mal-occurrence (i.e., mishap) insurance coverage that may be purchased on-line per transaction/medical event by a healthcare/medical service provider when providing a particular healthcare/medical service to a patient. The cost of this medical mal-occurrence insurance coverage is determined by factors such as historical provider outcomes, hospital outcomes, procedure complexity, patient complexity and other factors are made readily available on-line to an qualified insurance underwriter via the in the HME system databases. Different insurance underwriters may be asked to make online competitive offers to predetermined coverage parameters provided by the HME system so as to not confuse the consumer with small print coverage variations.

As also mentioned above, an another aspect of the exemplary on-line healthcare market exchange (HME) system and business method implementation described herein is that it provides or makes available through on-line transaction a medical warranty coverage insurance product that is tailored to cover such additional medical care expenses that result from unanticipated medical expenses encountered during performance of the specific purchased service (i.e., a single medical event/service). This medical warranty insurance coverage can either be purchased by the consumer or be built into the price of the purchased medical service. The price for warranty coverage for a specific single medical event may be determined by similar event-related statistics data available on-line to the underwriter from an HME system database. Multiple underwriters may be allowed to compete with each other online. Thus, the price for such health event warranty coverage might vary but the coverage criteria will remain invariable so that the consumer is not unduly confused by coverage variations among different underwriters.

Another aspect of the exemplary on-line healthcare market exchange (HME) system and business method implementation described herein is that it provides or makes available on-line a medical/health event-specific insurance product (i.e., insurance coverage for a specific health service) whose pricing is determined by statistical data or information contained and maintained in one or more of the HME system databases. Such data is made available to insurance product underwriters and may include, inter alia, accumulated procedural "outcomes" data for a particular healthcare service provider, a particular medical/health event, a particular hospital or specific service, pertinent medical complexity, provider and patient feedback data, location of service, etc. In this manner, a healthcare service insurance coverage for a mal-occurrence and/or warranty is provided that has a previously unprecedented accuracy for actuarial pricing as well as the option for allowing competing insurance product underwriters to offer their products (coverage) by means of their own proprietary pricing algorithms.

Typically, facilities providing medical services, particularly elective procedures, spend a significant portion of their operating budget on advertising and promotion. An important purpose of the advertising is to assure that the facility is fully utilized. The illustrative exemplary non-limiting implementation of an on-line healthcare market exchange disclosed herein provides an altogether different means for assuring efficient utilization of a medical facility. With the disclosed healthcare market exchange implementation, even if medical services were to be provided at a reduced price, the savings realized by reduced advertising and promotion can be shared with the patient, thereby reducing overall medical costs for the consumer and increasing profitability for the medical service provider. More particularly, the illustrative exemplary non-limiting implementation of an on-line healthcare market exchange disclosed herein provides a method and system that will enable prospective patients to easily identify and access an otherwise underutilized medical facility to negotiate a favorable fee for services subject to scheduling restrictions and other "specifications" set by the medical service provider. Likewise, underutilized medical facilities may now offer services at a negotiable fee in order to more fully utilize the resources of the facility.

Conventionally, most medical services are sold under a fixed-price protocol whereby the medical service provider sets a price for the service and a patient either accepts or rejects the price. The time, and sometimes the place, that the services are rendered in accordance with this protocol may be regarded as "flexible" in the sense that a medical service provider will typically establish a time and place (i.e., specifications) for rendering the service that is mutually acceptable to the parties. However, alternative protocols for perfecting buy-sell transactions between patients and medical service providers that are responsive to market forces, such as, for example, an auction or an exchange for buying or selling medical services similar to a stock exchange, have not been traditionally available.

Market research has indicated that people, lacking insurance for reimbursement of drug costs, typically pay as much as 15% more for a prescription medicine than people having such insurance for the same medicine. For example, seniors without drug coverage may not only lack insurance to protect against high costs, but may not have access to discounts and rebates that insured people receive. Uninsured persons may not purchase a needed prescription medicine simply because they cannot afford it. Moreover, market research indicates that spending for prescription drugs is currently growing at a rate that is twice that of other types of healthcare expenditures. This perceived inequity in pricing between insured and uninsured prescription medicine buyers now may be diminished by the on-line healthcare market exchange disclosed herein which seeks to provide a marketing system and method that enables the uninsured to buy prescription medicines at a "fair market price" that is both dynamic and determined as a result of competitive market forces. For example, overstocked medications that are to expire in six months may be sold at half price to those patients that can use them immediately.

The exemplary on-line healthcare market exchange disclosed herein more efficiently schedules personal physician procedures during known predictable slow times (for instance during the night) so as to better match medical resources with medical needs across geographic/time domains. For example, the exemplary on-line healthcare market exchange system also provides an automated arrangement whereby a doctor is enabled to first accept certain bid/cost proposals for his/her services and then decide whether to accept or decline the bid price (thus more efficiently and economically distributing medical services to desiring patients that might pay a lower cost because the procedure would be done during "off" hours or the like).

The illustrative exemplary on-line healthcare market exchange (HME) described herein may be implemented using a client computer system or suitable handheld wireless device comprising a telecommunications link to a remote medical transaction server via a digital communications network, such as the Internet, for enabling prospective buyers of medical services to negotiate with providers of medical services to identify and secure a reduced market-driven price for desired medical services. If desired, a condition may be imposed so that that the services will be rendered by the facility during a period of what would otherwise be facility underutilization. The illustrative exemplary on-line healthcare market exchange described herein may also be implemented using a programmed computer transaction system connected via telecommunication links to a digital communications network, such as the Internet, that enables a plurality of prospective sellers of medical services to offer medical services to patients, insurers and other third parties using an auction format. A minimum reserve price may be established for bids received using an auction format.

A buyer and seller of medical services can also communicate with each other to establish a mutually acceptable fee for services, the mutually acceptable fee being subject to a medical evaluation and restriction regarding the time and place where the medical services will be provided. Options may be provided in choosing a less convenient time and place for receiving medical services in exchange for a better price for his/her needed medical services. The qualifications of a medical service provider for the provision of an offered medical service may be authenticated. In fact a buyer and seller of medical services may have access to each other's respective transaction history and feedback history.

Another aspect of the illustrative exemplary on-line healthcare marketplace or market exchange (HME) implementation described herein disclosed herein provides a business method and system for providing an on-line auction of an option to purchase services (i.e., a service option). As an example embodiment, medical services and/or medical supplies (e.g., prescription medicines) may be offered for sale in an on-line auction forum subject to selected conditions that can be specified by a medical service provider such as, for example, the time and/or place where the personal medical service is to be rendered. In addition, the illustrative exemplary implementation of the on-line auction and health market exchange (HME) transaction system disclosed herein further provides a business method and system for providing an on-line auction of options to purchase services at a discount and/or analogous options. As an example embodiment, discount coupons to purchase proffered medical services at a discount may be placed up for auction on line by a medical service provider.

In addition, another aspect of the exemplary on-line healthcare market exchange transaction (HME) system implementation disclosed herein is that it will enable patients, whether insured or uninsured, to acquire elective surgical services, chronic rehabilitation services, medical equipment support, and other non-emergency medical and dental services through an auction format bidding process. Various covered and non-covered services such as podiatry, chiropractic, acupuncture, homeopathic, behavioral modification treatment and therapy, weight loss, hypnotherapy and other health related services may also be included for on-line listing and bidding in an auction format using the exemplary HME system implementation. Although many medically-related health services and products are subject to regulation to assure quality, the establishment of specific qualifying conditions and quality control measures are easily implemented by the HME system described herein.

An efficient arrangement is also provided for on-line solicitation of consumer feedback information from patients which, after being acquired, is maintained in a transaction database and made accessible to other prospective patients. The convenience of on-line availability of a consumer feedback database to prospective patients and other buyers of medical services should ultimately serve to improve the quality of medical services provided to patients.

Another aspect of the exemplary on-line healthcare marketplace or HME implementation disclosed herein is that a person desiring a specific medical service is provided with a means to identify a medical facility offering such services and can negotiate obtaining the services at a "preferred" price in return for agreeing to receive the services during a period of otherwise expected facility underutilization.

A yet further feature of the exemplary healthcare market exchange transaction (HME) system described herein is that it allows a "standby" option to be implemented wherein the performance of services are provided at a reduced rate to a buyer willing to accept treatment on a "standby" or delayed basis. This is particularly beneficial in that it provides a further component of cost reduction to the patient and/or his/her insurer and could provide the medical provider with greater assurance that revenue is not lost. Using the bidding/auction-type format, payment (either partial or full) may be made or secured electronically at the time a bid is accepted (rather than the customary 8-12 weeks after provision of a service, a basketful of paperwork and a plurality of phone calls).

A practical market-driven system that permits efficient buying and selling of medical services should also be subject to both strict quality control and acceptable practices by the medical community. Consequently, another aspect of the exemplary healthcare marketplace or HME implementation disclosed herein is that a medical service provider's qualifications are preferably authenticated/verified using an authentication engine prior to posting either a global or local offer to sell a service. In addition, an offer-acceptance agreement between a medical service provider and a patient may also be optionally qualified by a restriction that a patient submit to a medical evaluation to establish the appropriateness of the medical service for the particular patient.

Another feature of the exemplary healthcare market exchange transaction (HME) system described herein is that a qualified buyer of prescription and/or of the exemplary healthcare market exchange transaction (HME) system described herein is non-prescription medicines is permitted to post a proposal to buy medicine at a particular price, for example, via a database accessible to qualified vendors, and may also receive offers for sale of the same medicine from one or more qualified venders at a proposed purchase price.

Direct links to one or more transaction feedback databases are also provided to allow consumers of medical services to verify and evaluate a particular provider's product or service. The exemplary healthcare market exchange (HME) transaction system disclosed herein also allows for an agreement between a patient and a medical service provider to be conditioned on the establishment of medical fitness conditions of the prospective patient for receiving a particular medical service.

The illustrative non-limiting exemplary on-line healthcare marketplace or market exchange (HME) implementation disclosed herein further includes distinct auction transaction engine components for the purpose of supporting a separate on-line auction (i.e., separate from the professional medical services auction) for the auctioning of options to purchase proffered services at a discount (i.e., discount coupons) or analogous options for obtaining discounts that are redeemable against winning bid fees charged by a service provider for the proffered services. Using this aspect of the on-line HME system, a service provider has a choice of either providing a pricing profile listing proffered services with specific associated minimum bid prices on the services auction web-site or, if not willing to disclose a pricing profile or specific prices for proffered services, the provider may alternatively (or additionally) offer a discount coupon for specific proffered services on the associated discount coupon auction web-site. The exemplary on-line HME transaction also combines the use of distinct auction transaction engine components with the sharing of common database elements for further facilitating the on line auctioning of such discount coupons (and/or analogous options to purchase services at a discount) in cooperation with a separate on line auctioning system for products/services.

As still a further feature of the exemplary on-line healthcare marketplace or market exchange (HME) implementation disclosed herein is that it also provides a method and arrangement for implementing on line a person-to-person network marketing business model for rewarding existing member professional service providers for the recruiting of prospective new service provider members and for training them in the use of the on-line auction transaction systems described herein. A user network of training and rewards can similarly be implemented. This aspect of the HME system promotes the creation and development of a network of service provider members (and to a lesser degree purchases of health services) for the recruitment and training of additional service providers.

To provide an improved and enhanced overall on-line bidding experience to the consumer of a professional's services and to more effectively influence on-line offers made by professional service providers, the inventors realized that the on-line market exchange should also provide the on-line bidding consumer with an easy and convenient mechanism for arranging financing and paying for on-line bids. Accordingly, a financing and payment mechanism is provided in the form of a "health card" which, for example, may have the physical appearance of a conventional credit/debit card and may easily be implemented using a similar underlying infrastructure and technology. As an illustrative example, a health card may be integrated with the on-line medical services auction system and may also be customized with specific properties and limitations to make its use safe, secure, practical and feasible. For example, financing/payment of on-line bids may be accomplished through the use of the health card. Of course, any "health card" implementation as disclosed herein is intended to also incorporate any necessary security related and legal restrictions on its use such as, for example, restriction of its use to only health/medical related services and products.

The exemplary health card is preferably implemented in a manner that makes a variety of different financing options available to the member/user. Moreover, various custom financing arrangements may also be added as enhancements to the health card basic features. An integration of the disclosed example health card financing method and arrangement into the competitive pricing arbitration and on-line bidding system described in parent patent application Ser. No. 09/725,142, now U.S. Pat. No. 7,657,479, which is incorporated herein by reference, should act as a significant enhancement to the performance and market implementation of the overall system as described. The incentive is placed on an individual desiring to obtain non-emergency health services to at least make a few attempts to find determine the best price for an office visit or a consultation which he/she may require. The illustrative example health card mechanism and financing arrangements disclosed herein is intended to be used in conjunction with the disclosed networked on-line bidding system so as to aid a member/user in negotiating a best possible price for health services in a manner that makes the quality of the health/medical service provider fully transparent to the bidding consumer.

It is also intended that a robust variety of financing options are made available to a user of the health card. In the non-limiting implementation disclosed herein, some example financing options/arrangements made available to a user of the health card include: 1) use of the card to automatically draw against a user's HELOC (Home Equity Line Of Credit); 2) the card may used to draw against a user's life insurance cash value; 3) the card may be set up to automatically draw against death benefits of a life insurance polity; and/or 4) the card may be used to automatically access a user's Health Spending Account (HSA) or Medical Savings Account (MSA) maintained by an employer to finance qualifying health expenditures using pre-tax income dollars. Moreover, with this last example, the ability of a user/bidder to automatically access their HSA and/or MSA account to finance bidding and payment for rendered services further enhances the value of having an HSA and MSA. A still further aspect of the health card financing mechanism disclosed herein is that specific financing options and/or a particular pre-determined sequence for debiting payments from different accounts may be selected and/or programmed by the user/member on-line, for example, via a secure data link. When confronted with an unexpected and uncovered health event, an individual will have the option to raise money from variety of sources and literally shop for the cheapest available financing dollars.

Federal and state legislation now permits businesses and individuals to setup a health plan savings/flexible spending account. Such accounts are typically restricted in use to saving funds for medical expenses and health related services. One type of such flexible spending medical account attaches to the individual and follows the individual through different employers. Unused funds may accumulate and may be used in subsequent years. Funding for such accounts may come from pre-tax dollars contributed by the employer and/or the employee. For example, a portion of an individual's health savings/spending account may be funded by the employer and a portion by the individual account owner. Such accounts may generate interest income and growth but are restricted in use in that withdrawals from such accounts may only be used for paying health/medical related expenses necessary for maintaining the well being of the account holder.

Moreover, it is recognized that there is presently a growing trend of corporations offering high deductible insurance coverage to their employees due to the lower monthly premiums associated with this type of medical coverage. High deductible insurance provides full coverage to an employee and their family after a deductible ranging from $2,000-$5,000 (or greater if selected) is satisfied. Today approximately, 5% of corporations offer their employees high deductible health insurance. According to the Robert Woods Johnson Foundation, the number of corporations offering high deductible health insurance is projected to experience a 1400% increase over the next two years. Inherent to the increased offering of high deductible medical coverage is an increase of individuals required by their employer to self-finance a portion of their healthcare services. The federal government recognized this growing shift toward self-financing healthcare and, in response, passed legislation in January of 2004 creating a Healthcare Savings Account ("HSA") program for individuals carrying high deductible healthcare coverage. These individuals can open an HSA with a qualified financial institution and deposit pre-tax dollars in this investment account that remains with them year after year. They can also withdraw funds from this type of account without having to pay taxes when they use these funds for health related expenses.

The exemplary on-line healthcare market exchange (HME) implementation disclosed herein further provides a website where employees can negotiate preferred pricing with healthcare service providers (e.g., doctors, nurses, HMOs) for health services for which they are paying out of pocket. This negotiation opportunity reduces the amount of funds an employee needs to withdraw from his/her HSA thereby maximizing the value of these pre-tax dollars. Moreover, the exemplary on-line healthcare market exchange implementation disclosed herein achieves significant cost savings by continued use of on-line pricing arbitration between patients and health providers. Once the patient has reached their deductible for that year the HME insurance will reimburse or cover the patient for 50-85% of their negotiated health spending, depending on the coverage chosen. The patient remains in the driver seat of choosing their physician, and the proportional co pay provides motivation to negotiate with the health provider for best quality at best price. The health provider is competing against other providers on price and quality to capture the patient with a specific health problem. HME saves money by not having to have many negotiated contracts with multiple providers in multiple communities (a costly paperwork affair).

The patient negotiates best price from their chosen physician and the HME coverage plan spending is protected in part by the co-pay and in greater part by on-line market pricing of services free of processing costs. In this regard, the inventors believe that if doctors are allowed to treat patients and receive immediate payment or prepayment, are spared from labyrinthine processing and billing delays, they will offer significant cost savings to patients and subsequently to HME as the insurance underwriter for spending beyond the deductible fence. The patient benefits from choices, the provider negotiates with the patient, and health spending is controlled by the patient and not by a third party interested in profits, increased premiums and denial of care. Consequently, the exemplary HME implementation disclosed herein is arranged to make healthcare services easily accessible to all including the uninsured, the "deductible" market and those having an HSA program.

The exemplary on-line healthcare marketplace or market exchange (HME) implementation disclosed herein enables individual on-line users, employers, finance brokers and insurers to find, evaluate, compare, negotiate and bid on the purchase of health care services and products. The exemplary HME also provides on-line users with access to comprehensive information on treatments and detailed profiles on medical service providers, including clinical abilities and the minimum bidding prices for the different types of professional services/procedures offered.

In a more general economic context, the disclosed exemplary implementation of an on-line healthcare marketplace/market exchange (HME) provides an efficient apparatus and method for exerting market forces on the costs of delivering professional services and for streamlining potentially costly administrative procedures associated with providing such services. The on-line HME business method and system disclosed herein enables free market forces to play a part in the negotiation, optimization and determination of medical service value while facilitating the connection between physicians and cash paying patients. The on-line HME is a market-driven, price and quality automated arbitration system and method that interfaces well with the uninsured, the underinsured, and the self-insured patient populations so that these individuals can benefit from competitive healthcare pricing.

BRIEF DESCRIPTION OF THE DRAWINGS

These and other features and advantages provided by the exemplary health market exchange transaction and medical services auctioning system disclosed herein will be better and more completely understood by referring to the following detailed description of presently preferred embodiments in conjunction with the drawings, of which:

FIG. 6 is a block diagram illustrating non-limiting example functional processes and features available to an on-line visitor upon using/accessing the on-line auction transaction and healthcare market exchange system (HME);

FIG. 12 is an image of a non-limiting example Internet page for procuring dental services using the exemplary on-line auction transaction and healthcare market exchange system (HME);

FIG. 13 is an image of a non-limiting example Internet page for procuring personal medical services using the exemplary on-line auction transaction and healthcare market exchange system (HME);

FIG. 14 is an image of a non-limiting example Internet page for procuring other alternative medical services using the exemplary on-line auction transaction and healthcare market exchange system (HME); and FIG. 15 is an image of a non-limiting example Internet page for procuring Veterinary medical services using the exemplary on-line auction transaction and healthcare market exchange system (HME).

DETAILED DESCRIPTION OF NON-LIMITING EXAMPLE EMBODIMENTS

A non-limiting description of an exemplary on-line health market exchange (HME) service method and system is provided herein. The disclosed exemplary HME service method and system, in addition to hosting an on-line medical services auctioning system, includes interactive tools for arranging financing of successful bids, performing on-line research of proffered services and providers, as well as participating on-line in other healthcare related negotiations and transactions. The on-line HME system provides an Internet accessible web-site that acts as a "one stop" full service on-line marketplace for use by healthcare service providers and prospective consumers/patients for negotiating and consummating transactions for proffered medical/healthcare services and products. The on-line HME service provides Internet access to customized proprietary databases and interactive tools for obtaining credentials information and for conducting on-line research concerning prospective healthcare service providers/facilities, and for making on-line payments/arrangements for healthcare/medical service financing. A personal "health-card" product and service, analogous to a conventional debit/credit card, is supported by the HME service and made available to eligible members/users. On-line resources for reviewing and procuring various types of insurance coverage for performed medical services are also made available.

Figure 1A:
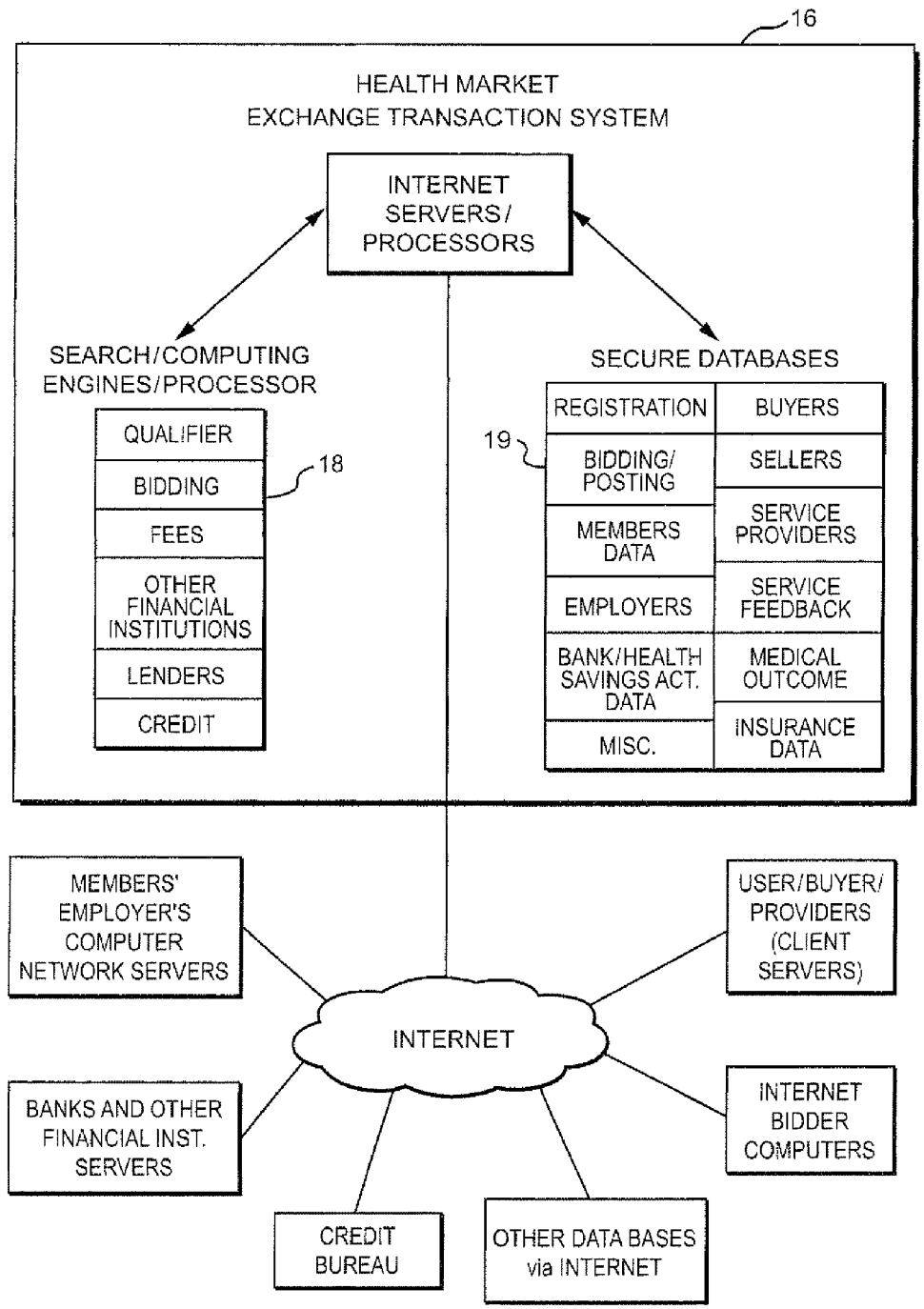
FIG. 1A is a high level block diagram illustrating a non-limiting example Health Market Exchange (HME) transaction system.

FIG. 1A is a high level block diagram illustrating an example Health Market Exchange (HME) transaction system network server 16 for conducting on-line auctioning for human and animal medical services, conducting service provider quality research, arranging financing and other transactions related to the procuring of medical services and products. The HME transaction system 16 may include one or a plurality of Internet servers or processors that comprise one or more search and/or computing engines 18 and secure databases 19. The search/computing engines 18 include servers and computing engines for handling on-line bidding, providing provider qualifying tasks, fee handling tasks and performing secure communications and interfacing with on-line bidders, health service providers, bidders' employers, as well as other corporate entities, financial institutions, lenders and credit reporting organizations. The HME transaction system 16 also comprises a plurality of different types of databases 19 for conducting transaction operations including, for example, secure databases for maintaining user related registration data, information concerning buyers and sellers, service providers, employer data, members data, service feedback information from users, medical outcome data/statistics for on-line researching, insurance provider information, as well as bank/financial institution and health saving account data. The HME transaction system 16 preferably uses the public Internet as a primary communications backbone but is not intended to be restricted or limited to this network of form of communication alone (e.g., the use of private communication networks as well as wireless communication networks is also possible and contemplated as a supplementary or alternative communications backbone). As illustrated in FIG. 1A, the use of the Internet and/or other networks allows easy and efficient communication with and between a large variety of entities including, for example, individual user/bidders from home computers, various medical service providers and health organizations, bidders/members' employer's networks, banks and many other commercial/financial entities, etc.

Figure 1B:
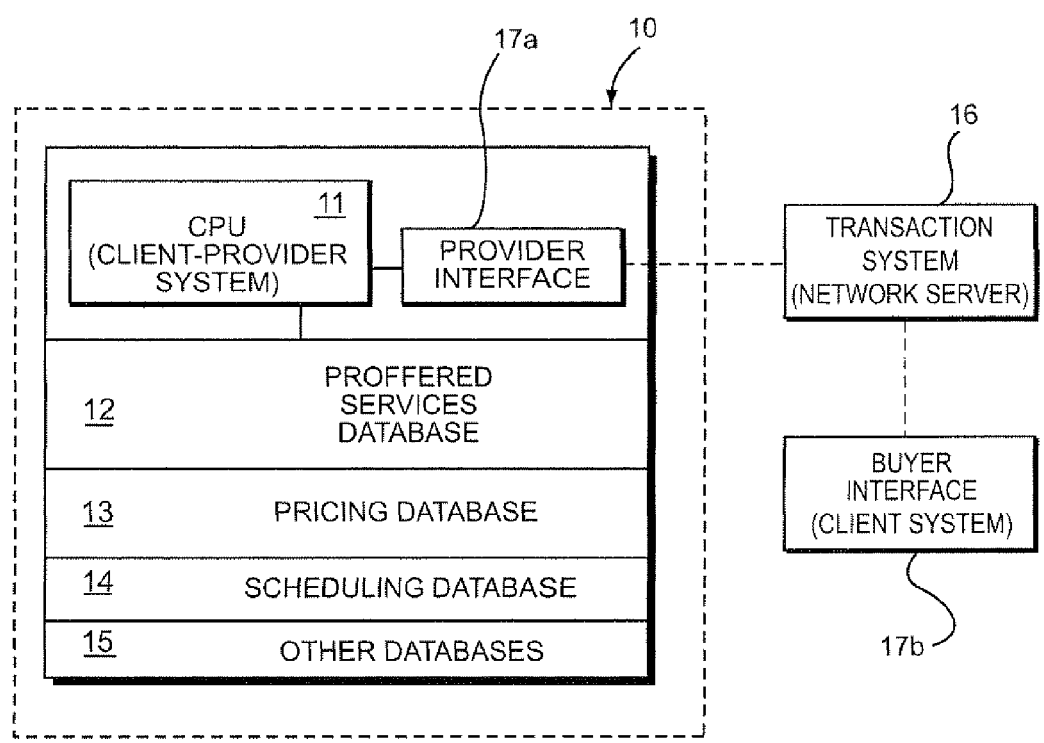
FIG. 1B is a block diagram illustrating an example client-server arrangement for an on-line auction transaction and market exchange system (HME) and an example service provider computer system arrangement.

In FIG. 1B, an example client-server arrangement for the Health Market Exchange (HME) on-line marketing/auction transaction system is illustrated along with an example of a health service provider's computer system arrangement that may be in communication with the HME via the Internet. The service provider's on-line client-server computer system 10 includes at least one central processing unit (CPU) 11 and a plurality of data bases 12 through 15 which may be maintained on one or more data storage devices. In this illustrative example, CPU 11 may be connected to, among other things, a proffered services database 12, a pricing database 13 and a scheduling database 14. CPU 11 utilizes information stored these databases to compute and post offering prices for proffered services available over/within/during certain predetermined set time periods for/at specific geographic locations. Other databases 15 may also be used to store, among other things, service provider credentials/licensing information, user/customer credit information, insurance company data, customer/provider feedback information, in an offering price database 15. CPU 11 (which may actually comprise multiple servers or a network (cloud) of Internet servers) functions as a management server for managing Internet web pages for the HME and for transferring (e.g., posting or uploading) data from the databases 12-15 to one or more HME web-page servers comprising the HME transaction system 16. A prospective online consumer of proffered services may likewise be connected to the HME web-page server computer transaction system 16 via digital communications interface and a personal commuter system 17b. For the purpose of the present description, information transferred from the provider may be collectively referred to as "specifications" for the proffered service. Such transferred specifications data may comprise, for example, scheduling information, credentials information, competitive pricing information, and/or information concerning the specific service provider and services being offered and/or a minimum asking/bid price for the proffered service.

Figure 2:
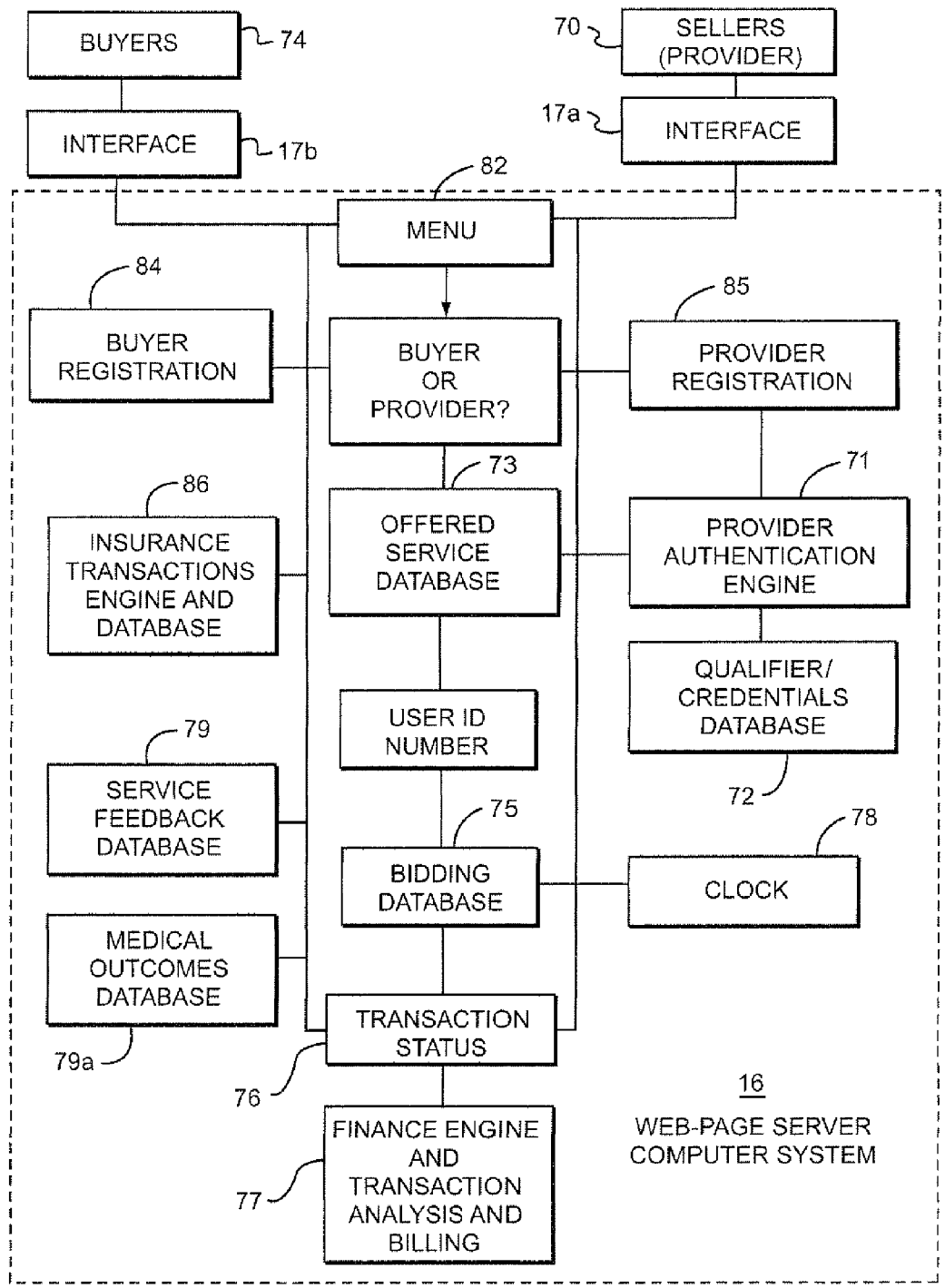
FIG. 2 is a block diagram illustrating a non-limiting example on-line auction transaction and healthcare market exchange system (HME) for service providers and customers/bidders of proffered products/services.

FIG. 2 is a block diagram illustrating an exemplary HME web-page server and computer transaction system 16 that is operable to provide a comprehensive on-line (i.e., the Internet) healthcare services marketplace for researching healthcare services and for conducting buy-sell and/or other auction-type transactions between a service provider/facility and patients desiring to buy such services. Although a single example transaction is disclosed wherein a service provider offers a specified service for sale at a preferred price and the offer is presented to a plurality of buyers for acceptance by a single buyer, a practitioner of ordinary skill in the art will realize that web-page server computer transaction system 16 may be used to implement many different types of marketing and auction transactions.

A specified professional/licensed service and associated price contained in an offering price database of a service provider's credentials/qualifications, services and other information (as shown in example FIG. 1B) is transmitted to web-page server computer transaction system 16 via service provider-controlled interface 17a (which may comprise, for example, a keyboard/CPU/modem/telecom circuit or other conventional computer networking devices). Prior to posting the offer for sale, transaction system 16 prompts the provider (seller) 70 to enter a registration identifier. If the provider is not registered to offer services for sale on the system, the provider must register on-line. In order to register, the provider must identify himself/herself and enter one or more professional/licensed services that the provider is qualified to render. The provider's qualifications for performing the stated professional/licensed services are authenticated by means of a search engine 71 having a direct link to a qualifier database 72 and/or hyperlinks to one or more other qualifier databases 72.

Generally, as used herein, the term "search engine" means an apparatus (or method) automatically operable for receiving a user generated label, searching a directory comprised of one or more databases for a matching label and identifying databases within the directory which contain a matching label. The term "qualifier database," as used herein, means an electronically accessible computer-readable storage medium containing authentic certification data for professional/licensed service providers. Some examples of qualifier databases include the AMA's membership roster, a State Medical Licensing Board's roster of licensed physicians, the American College of Surgeons roster of board certified surgeons and a roster of Board Certified Plastic and Reconstructive Surgeons, as well as specific hospital staff privileges roster. If the professional/licensed service provider is qualified to render the professional/licensed service being offered, the qualifications are authenticated by the system 16 and the provider-transmitted service and offering price data, including any restrictions (specifications) are accepted by the system 16 as a conditional offer for sale. Put another way, a statement of an intention to offer specified professional/licensed services for sale at a specified date and time, or range of dates and times, at a specified price is posted on an offered service database 73.

A plurality of patients ("buyers") 74 gain viewing access to the posted data via a patient interface 17*a* (e.g. via the Internet). If the conditional offer for sale is acceptable to a patient (or other buyer such as a patient's insurance company) who is a registered user of the system 16, the patient/buyer submits his/her offer to buy (bid) by on-line posting on a bidding database 75. If the offering price of the professional/licensed services, which offering price is included in the specifications of the offer to sell the professional/licensed service, is "fixed", that is, not open to negotiation, the bid is compared with the offering price and, if a match occurs the bid is accepted and the transaction recorded in a transaction status storage device 76. If the consumer demand for the service at the posted "fixed" price is greater than the number of services offered at the "fixed" price, other bidders can bid the price higher to gain priority for the limited service at the "fixed" price (Dutch Auction).

The HME web-page server computer transaction system 16 notifies the buyer and seller that the transaction is complete and the registered buyer and seller identification and transaction selling price entered into a transaction analysis and billing database 77 wherein the parties to the transaction are billed for system use. The buyer and seller may then communicate directly in order to satisfy specifications posted by the provider such as scheduling a medical exam and arranging to have required lab work done prior to the time the professional/licensed service is to be rendered.

The HME web-page server computer transaction system 16 is capable of receiving offers to purchase particular a posted professional/licensed service in a serialized fashion so as to enable the professional/licensed service facility to accept only those offers for which it can reasonably expect to provide consideration and reject buy offers received after 100% facility utilization is realized. Accordingly, clock 78 records the time that an offer to buy is placed to prioritize such bids. Higher bids (i.e. bid purchase prices exceeding the "fixed" price) may receive priority over a lower, but otherwise acceptable, bid which is received earlier. After the professional/licensed service provider's facility schedule is full for specified dates and times, additional patients' buy offers (bids) are either rejected or may be accepted by the professional/licensed service provider on a "standby" basis for other future slots.

In any practical buy-sell system, whether market-driven or otherwise, the professional/licensed service provider must have the ability to bind a patient to a legal contract under the terms of the patient's offer to purchase. Similarly, the patient must have the ability to legally bind a professional/licensed service provider to the terms of the professional/licensed service provider's offer to sell. Accordingly, transaction system 16 provides a registered prospective buyer/purchaser of medical/healthcare services with access to quality assurance information relating to the necessary qualifications that a service provider much have in order to provide the particular medical/healthcare service. Such information may include, inter alia, state and federal statutory regulations concerning medical/healthcare service providers, required qualifications and board certifications, applicable hospital privileges, etc.

Figure 3:
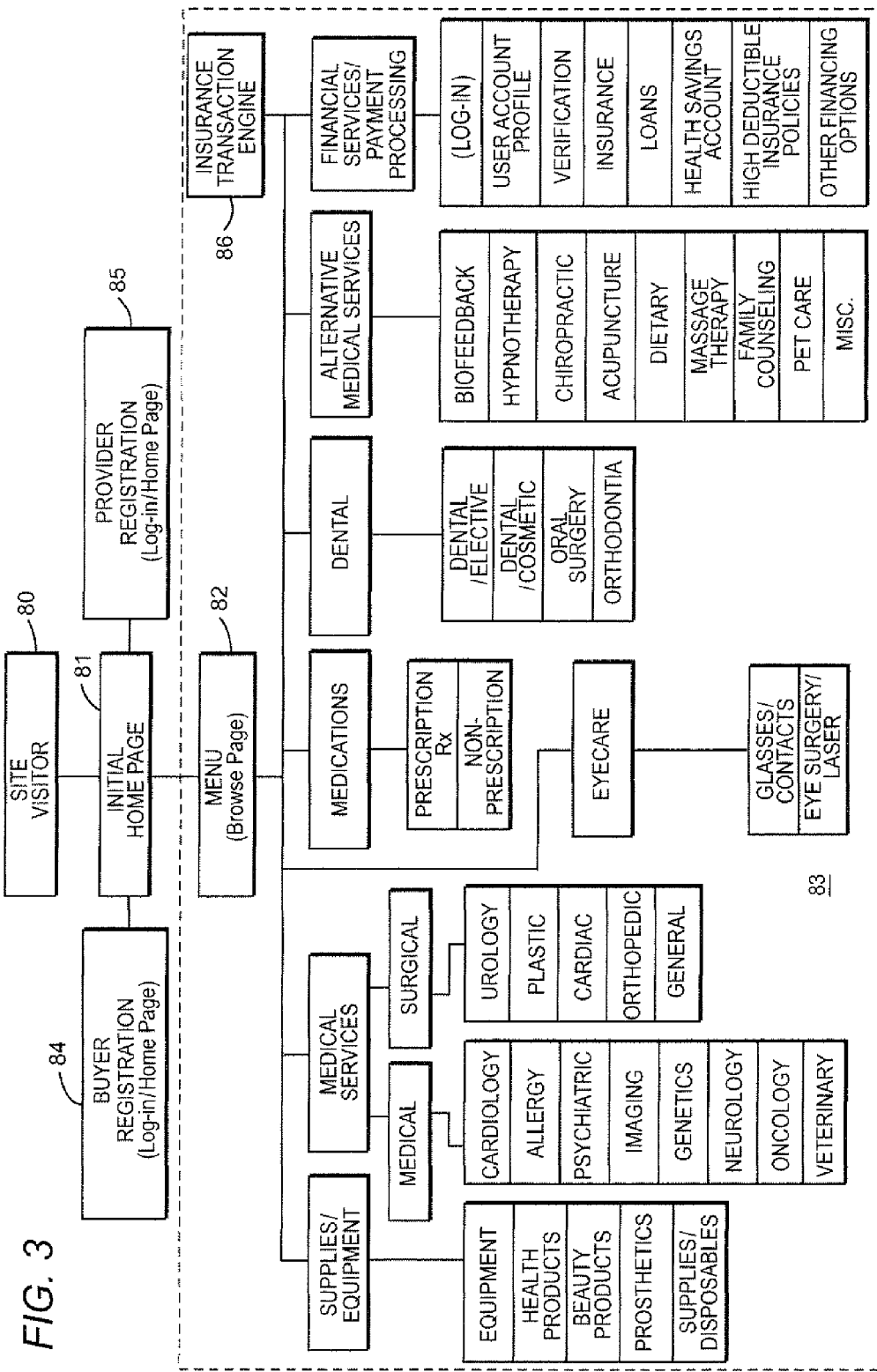
FIG. 3 is a block diagram illustrating a non-limiting example organizational relationship of user interface browser web pages for the on-line auction transaction and healthcare market exchange system (HME)

Depicted in FIG. 3 is a schematic diagram of a non-limiting illustrative example Internet accessible web-site "home page" or "main page" having, for example. This web-site is made available on-line by transaction system server 16 connected to the Internet for enabling public access and browsing of the healthcare/professional/licensed services marketplace exchange (HME) transaction service discussed and disclosed herein. An on-line visitor (80) to the site, who may be either a prospective buyer or seller, is directed to the home or main page screen 81 and identifies himself/herself/themselves as either a buyer, a seller, or payor, (e.g. an insurer) of professional/licensed services/products, and provided with a menu 82 displaying a variety of medical related services and product options, including options for buying or selling professional/licensed services, medical equipment, and medical supplies such as drugs. The visitor 80 may browse various menu-linked web-pages and associated databases by selecting displayed links 83 of different products and services. If the visitor wishes to bid upon or buy or sell a proffered professional/licensed service or product, that visitor must first participate in an on-line registration process and complete either a buyer/bidder registration questionnaire 84 or a service provider registration questionnaire 85. Prospective buyers/bidders and healthcare/professional/licensed service providers then may be subjected to a credit and/or professional credentials evaluation based upon such registration information.

The term "healthcare/professional/licensed service", as used herein, includes surgery, medicine, radiology, medical equipment sales or leasing, pharmacy, alternative medical services, dentistry and dental procedures, rehabilitation services and other healthcare/medical services, the provision of which may be subject to various Federal and/or state licensing requirements. The disclosed method for providing an on-line healthcare/medical exchange (HME) service depends, at least in part, upon enrolling at least one, and, preferably a plurality of reputable healthcare/medical service provider(s). This is process is facilitated by providing a secure on-line registration process for obtaining identification and credentials data and subsequently maintaining that information in a secure database (FIG. 2). After a healthcare/professional/licensed service provider is enrolled, that provider may request the HME web-site server system 16 to post an offer to sell a particular professional/licensed service or product. That service or product is then listed within the HME web-site menu 82 along with a corresponding specified offering price. An insurance product web-page 86 and associated database and transaction engine is also provided to display various insurance products and related information (e.g., historical medical procedure/service outcome data) and to make such products and information available on-line to both registered healthcare/professional/licensed service providers and on-line buyers/bidders.

Referring again to FIG. 2, web-page server computer transaction system 16 authenticates the qualifications of the professional/licensed service provider by searching a Qualifier database 72. This Qualifier database includes every service listed in the menu of professional/licensed services along with licensing requirements for providing the particular service. The Qualifier database 72 may also contain a list of professional/licensed services, the qualifying requirements for rendering such professional/licensed services and hyperlinks to databases storing the identification of professional/licensed service providers having satisfied a particular qualifying requirement. If the provider's qualifications for performing a particular service have not been previously authenticated by the system, a software qualification engine will access and search external databases that identify qualified providers for the particular professional/licensed service.

In a non-limiting example implementation of the qualification engine, a medical specialty Board Certification awarded to a given practitioner is used to define the cluster of CPT coded procedures that the practitioner may perform well. If a practitioner posts a procedure or service for bids for which he/she is not duly certified, an internal alert is raised by the qualification engine and a request for specific qualifications is made to practitioner. In this manner, the qualification engine prevents a cardiologist, for example, from posting a body liposuction as a procedure for soliciting bids. Moreover, the qualification engine may implement this and other predetermined restrictions using an evolving list of threshold qualifiers for accommodating orphan procedures practiced by the various medical specialties.

Once the qualifications are authenticated, an offer to sell the specified professional/licensed service and the specified offering price is posted on a global database 73 that is accessible, on-line, to a plurality of buyers. For posting purposes, the system uses a basic qualification threshold. It may be desirable to provide means for the patient to access additional provider qualification to bolster the bidder's comfort with placing a bid. The system will prevent a dentist from posting an offer to perform a liposuction procedure but will not prevent a general surgeon (legally qualified) from offering such services. A provider's membership in the American Liposuction Society will be reassuring to the prospective bidder but such membership will not define the gateway to performing such a procedure.

The illustrative exemplary non-limiting implementation of the described on-line health services marketplace system presented herein provides free system access to a plurality of prospective buyers for the purpose of viewing offered professional/licensed services. In order for a prospective buyer to purchase a listed service at a listed purchase price, or at any price, the prospective buyer of professional/licensed services must first enroll using an on-line registration system. 84 (FIG. 2). Once enrolled (registered), a buyer is issued a buyer identifier and, using the identifier, may place an offer to purchase the listed professional/licensed service. The system receives the offer to buy, accompanied by a specified purchase price, from the buyer, and if the specified purchase price in the offer to buy the specified professional/licensed service is greater than or equal to the last bid price, the offer is accepted and stored in a transaction status database 76. The transaction status database 76 includes a processor that provides an output to the seller identifying the buyer and enabling direct communication therebetween. The parties to the closed transaction are then billed for system use via the transaction analysis and billing processing unit 77 (FIG. 2).

The exemplary on-line arrangement for buying and selling medical/healthcare services, described above, is efficient and has advantages realized by both the buyer and the seller. The seller can reduce advertising costs and use facility resources more efficiently. The buyer secures needed or desired professional/licensed services by accepting restrictions regarding when and where the service is provided as set forth in the specifications accompanying an offered professional/licensed service. The method may not in all instances, however, fully bring market forces to bear on the pricing of professional/licensed services. In the above example, the price is set by the professional/licensed service provider either at a "fixed" price or at the highest price proffered in a Dutch auction, and is either accepted or rejected by the buyer. The goal of fully bringing market forces to bear on the pricing of professional/licensed services is better realized by opening the price of professional/licensed services to competitive bidding, most preferably in the form of an auction.

The above-described method for selling and acquiring professional/licensed services at a fixed price may be modified by posting offers to sell professional/licensed services on a global database at an open, unspecified price that exceeds a fixed minimum reserve price. In at least one example implementation, the enrollment and authentication of buyers and sellers is performed as described above. The professional/licensed service provider (seller) submits an offer to sell specified professional/licensed services at a price to exceed a minimum reserve price. After the system 16 receives the offer and authenticates the professional/licensed service provider's qualifications to provide the professional/licensed service in the manner described above, the offer to sell is posted on a globally accessible offered service database 73.

A plurality of registered buyers 74 (FIG. 2), viewing the offer to sell, may submit an offer to buy the offered professional/licensed service. The purchase offer and the time that the offer is received by the system are stored. The proffered purchase price, specified in the offer to purchase, is compared with the reserve price specified by the seller. If the proffered purchase price is equal to or greater than the reserve price, the purchase offer is entered into the bidding database and the time that the offer was proffered is recorded. A second prospective buyer may view the first buyer's proffered offer and submit a second offer to purchase the professional/licensed service at a price that exceeds the price offered by the first prospective buyer. If the purchase offer proffered by the second buyer is greater than the price proffered by the first buyer, the offer proffered by the second buyer is entered and the first buyer notified that a higher bid was received. The first buyer, or any other buyer viewing the second buyer's offer, can proffer a third offer that exceeds the then-current highest offer. The process continues until the time allocated for closing the transaction, specified by the seller, has been reached, and further bidding is closed. As in the seller-set price example described earlier, the parties to the transaction are notified that the transaction is complete and then they are billed at 77.

The provider feedback database 79 (FIG. 2), provides means for the buyer to comment on the transaction after the professional/licensed services are rendered. Buyer comments providing feedback regarding provider performance are stored in the database 79 for future reference. A historical record is developed consisting of all data and information relating to the post procedural results of the medical/healthcare service received by each patient from each provider. Since a medical "outcomes" database as such may take some time to develop and acquire meaningful data, it is stored as a partition of transaction feedback database 79 or as a separate database. Accordingly, a professional/licensed service/procedure "outcomes" database 79A is also provided for inputting and archiving such information.

The exemplary web-page server computer transaction system 16 also may include an insurance transaction engine and database 86 for providing resources to users/patients for acquiring various types of insurance products on-line via the HME system web-site.

An Example Implementation Of The Bidding Negotiation Process

A prospective purchaser (user/buyer/bidder) of health services accesses and logs on to the HME website (e.g., PriceDoc.com) and searches for providers within his desired location that offer discounts on their services. The healthcare/professional/licensed service providers independently register with HME system and submit their qualification information which is then cross-referenced by the HME system against the databases of the appropriate medical profession qualifying entities. The prospective buyer may search by location, by doctor, by procedure, by hospital, by time of service, by price range. The prospective buyer may also review the credentials of the provider on-line as well view the comments/feedback of other patients in order to narrow his choices. The HME system website also provides verification of claimed credentials via a searching or cross-referencing of information with the appropriate professional credentialing institutions. The buyer may now exercise an immediate purchase option at the listed price or enter a time-limited bidding strategy to secure a lower price determined by presence or absence of other competing bidders for the services of a given provider. Upon winning the bid the buyer can purchase the option to lock-in a specific procedure with a specific provider for a specific price. As an example, the buyer may have obtained a purchase price of $725 for a tonsillectomy that normally lists for $1800. The buyer pays the option purchase price of $30 to the on-line HME (e.g., PriceDoc.com) at time of bid and pays the surgical costs to the professional/licensed service provider at time of service. Alternatively, the buyer can prepay outright the $725 to the on-line HME, which will than prepay $695 to the provider and the provider would have therefore paid the $35 option fee on the behalf of the patient. Notably, many physicians may feel some discomfort having true pricing profiles for proffered procedures fully disclosed due at least in part to fears that insurance companies may use such data to lower provider reimbursements even further. Consequently, the on-line HME system website is also set up to allow each provider to offer a discount coupon for a cash prepay patient that can than be used in lieu of partial payment against an undisclosed office price for a given procedure. If for example a provider is offering a $900 discount coupon for a cash paying buyer for a tonsillectomy, the buyer per example may purchase such a coupon on-line at the HME system website for $40 via an "instant buy" option or for $32 via a bidding process. When the provider of services is receiving his payment for a procedure (tonsillectomy) for which he normally charges $1800 (but more often receives or accepts only $640 from the patient's insurance company after substantial delay), he accepts the $900 discount coupon in lieu of partial payment and the patient than pays the remaining $900 from his HSA or MSA account (or other personal financial resources). This arrangement allows medical/healthcare service providers to offer significant discounts to cash paying patients yet preserve their pricing profile confidentiality and avoid the perception of converting personalized health care to a negotiated commodity. In this manner, patients may gain a pre-negotiated discount from their favored provider, the provider gains a new cash paying patient, and the prevailing perception that health care is not a "commodity" is at least partially preserved.

Another aspect of the exemplary healthcare marketplace system implementation contemplates purchasing of professional/licensed services at a price determined by prospective buyers. In this example, a registered user 74 logs onto the system 16, selects a professional/licensed service that he/she wishes to acquire and proffers a purchase price for the professional/licensed service. If the user is a valid registered user, the purchase offer is posted in a "services wanted" bidding database 75 which may comprise one or more constituent databases such as, for example, a seller-set price database (93) and a buyer-set database (94). The bidding database 75 is made accessible to registered providers of professional/licensed services and if a provider that is viewing posted offers to buy wishes to provide the particular professional/licensed service at the proffered seller-set price, then the professional/licensed service provider submits an offer to sell the specified service to the system. After the professional/licensed service provider's qualifications for providing the professional/licensed service are authenticated by the system, the offer to sell is posted for viewing by the user/buyer. The user may then either accept the offer and all conditions specified in the offer, such as the location and date that the services will be rendered, or defer acceptance of a particular offer until a specified time. Further offers to sell professional/licensed services to the user/buyer may be submitted by qualified sellers until the time window specified by the user for receiving offers closes. The user may accept or reject any professional/licensed service provider's offer to sell without cause.

Figure 4:
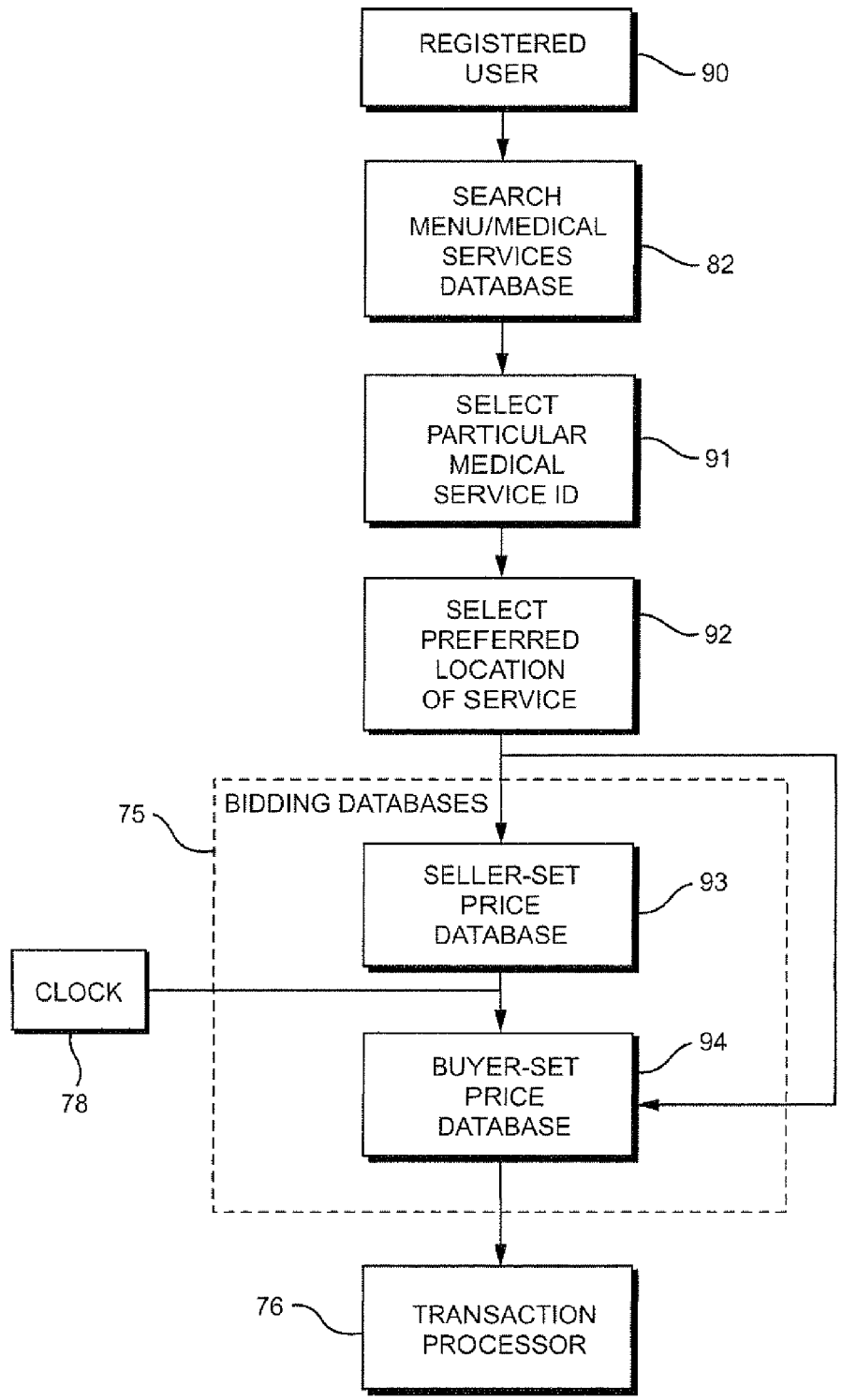
FIG. 4 is a block diagram illustrating a non-limiting example of an interactive relationship between different functional aspects of an exemplary on-line auction transaction and healthcare market exchange system (HME)

Any user/buyer, once registered, whether a patient, an agent of the patient or an insurer, may use the health services marketplace system 16 to bid for an offered professional/licensed service. The registered user/buyer may also use the system to post an offer to purchase a specified professional/licensed service and solicit bids for the specified professional/licensed service from professional/licensed service providers. With reference to the example diagram shown in FIG. 4, a registered user 90 is linked to a menu 82 of professional/licensed services (shown in more detail at 83 in FIG. 3). The registered user/buyer 90 selects a particular professional/licensed service 91 from a menu/professional/licensed services database (82) and is prompted to identify a location at 92, by city and state, where the particular professional/licensed service is to be rendered. The registered user/buyer is then provided with a choice of ways for offering to buy or sell the particular professional/licensed service 91. For example, a user/buyer may scan for offers to sell a particular professional/licensed service in the geographical area of interest that are posted on the bidding database. The user/buyer can either purchase the professional/licensed service at the price specified by the professional/licensed service provider or proffer a purchase price that is less than the specified selling price. The user/buyer's bid is compared with the highest previous bid received from other user/buyers which is stored in the bidding database and either replaces the highest bid in the bidding database or is rejected. The bidder is then notified on-line of the previous highest bid prior to entering a bid thereby providing the opportunity to increase the bid. A time-out clock 78 is maintained by the HME system bidding engine server to time-stamp the posting of bids and for setting a predetermined time limit for accepting bids for a particular item/service.

If the professional/licensed service provider has specified a minimum reserve selling price which is greater than any user/bidder's offering price then, at the user/bidder's option, the offer to purchase may be posted to a Buyer-set price database (94) and the user/bidder's offer to purchase will be made available on the HME web-site for viewing by registered professional/licensed service providers. A professional/licensed service provider viewing the particular user/bidder's offer to purchase at a set price may, in turn, either accept the user/bidder's set offer or proffer a new or counter offer specifying new or specific conditions which is then stored by the HME system to a Seller-set price database (93). The prospective buyer (the user/bidder) is then notified of the counter offer and associated conditions (e.g., via email) and may then either accept or reject it by responding through the HME web-site. Clock 78 may also be used to time-stamp Buyer-set and Seller-set postings in the database.

An Example Implementation Of The HME Web-Site

Figure 5:
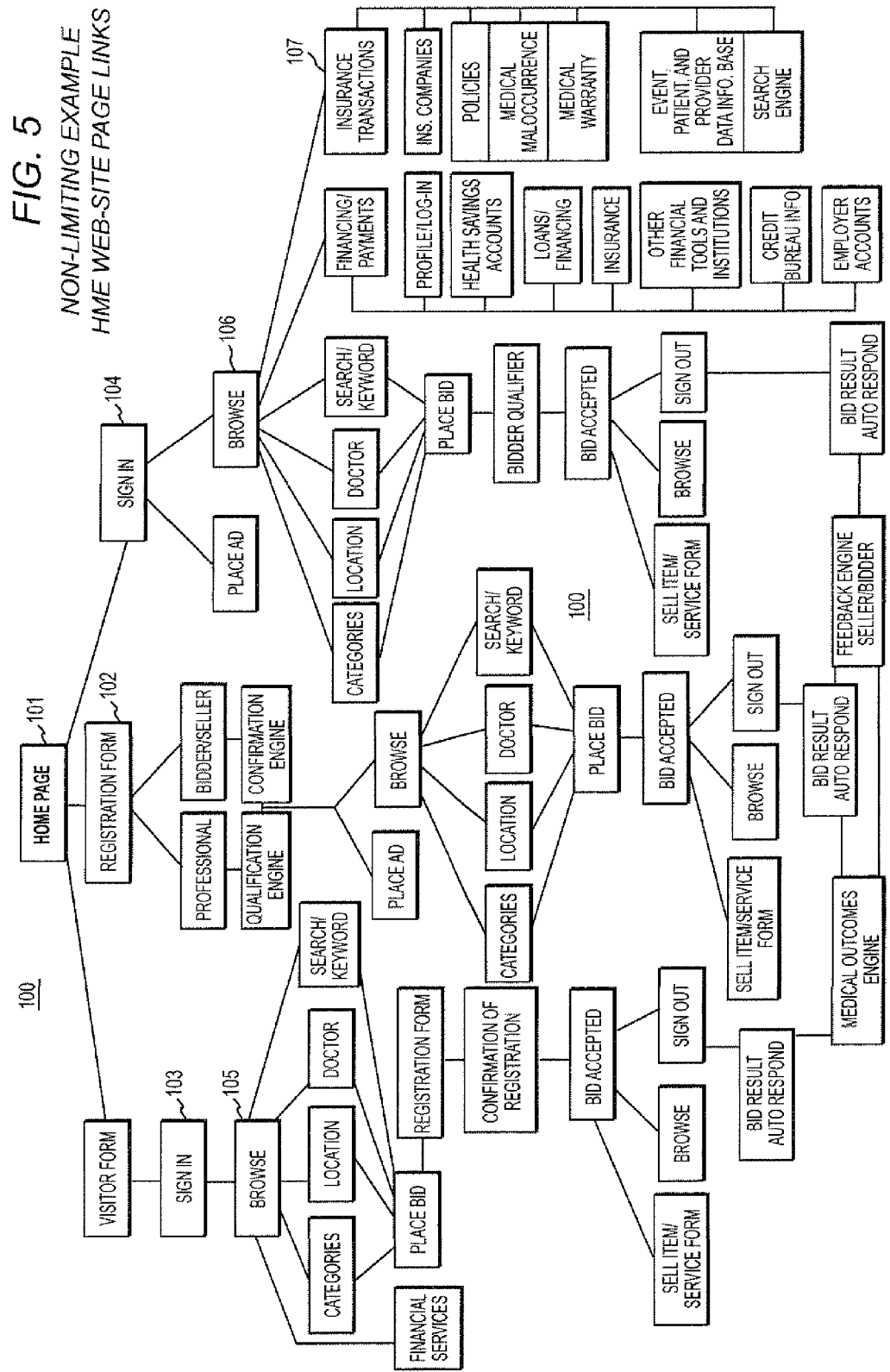
FIG. 5 is a block diagram illustrating a non-limiting example of linked web pages accessible on-line via a web-site starting/home page of the exemplary on-line auction transaction and healthcare market exchange system (HME)

FIG. 5 shows a hierarchical diagram providing an illustrative exemplary non-limiting implementation of linked Internet "web" pages, illustrated as labeled blocks 100, for an example on-line healthcare marketplace and professional/licensed services transaction system "web-site" provided by transaction system 16. Any person having a computer with an Internet connection and a conventional "browser" program can obtain access to the HME transaction system web-site. In this example, conventional HTML document "web" pages 100 are distributed via the Internet by transaction system 16. Hyper-text links (not shown) on the web pages allow an on-line "visitor" to view further web pages provided by medical transaction system 16 (as indicated by the connecting lines between labeled blocks 100). The various web-pages may be accessed, for example, by prospective bidders and service providers via the hyper-text links for obtaining specific information or performing a particular function. For example, an on-line "visitor" to the transaction system website may begin an on-line session by receiving a "home page" 101 from which the visitor can access and view other "linked" pages for participating on line in selected transactions and related activities such as, inter alia, registering via an interactive on-line registration process (102), verifying identification as a registered user via "sign in" pages (103, 104) or browsing other healthcare related information (105, 106) via key-word or various category specific links or for researching and purchasing various proffered healthcare/professional/licensed service related insurance products (107).

FIG. 6 shows a relational information diagram 200 illustrating related functional processes and features available to an on-line visitor upon accessing and using the on-line healthcare market exchange system (HME) web-site. Various on-line databases, service provider ID and credential researching tools, on-line auction features and automated financial transaction features, inter alia, are all available to an on-line visitor 201 upon accessing the HME web-site. For example, upon accessing the HME web-site, an on-line visitor, member or user such as, for example, a prospective bidder, a professional/licensed service provider or a provider of financial or other services (e.g., an insurance company/provider) first encounters one or more on-line registration forms. Preferably, an on-line registration is required before the system allows the user/visitor to proceed. On-line registration forms provided to a provider of healthcare services (who are required to provide the HME system with its professional qualifications information before being allowed to proffer such services over the HME) are different than that provided for a buyer of services—who, for example, are required to provide sufficient personal identification information to allow the HME to establish credit worthiness so as a to make them a credit able purchaser of services. This may be accomplished through the use of conventional on-line credit checking engines having links, for example, to VISA, Mastercard and other credit or banking institutions. A prospective purchaser of services may then access a "posting" database web-page 202 where procedures for bidding are made available to registered bidders and where service providers can post their proffered services and any specific conditions for retaining them.

In this particular non-limiting example, there are web page links 203 from posting database page 202 that link to individual provider web-sites to enable further research into the qualifications of various service providers. There is also provision for making an e-mail connection 204 with the proffered service providers if there are specific issues that need to be answered or negotiated between a bidder and a particular service provider. Access to a search engine 205 is also provided which can search HME topics and transactions by specific category, time, location, and proffered service, as well as various parameters relating to quality assurance of proffered services. For example, a database 206 containing quality assurance information may be linked to a database 207 containing information concerning registered HME service providers. Additional web-pages, links and databases are also provided for, inter alia, posting and viewing individual comments/feedback associated with various HME transactions and researching medical procedure/service outcomes. For example, links to a software qualifier/credentials authenticating engine 208 is provided for evaluating registered service providers using information obtained via Internet links to other agencies and entities such as the AMA, official state and federal licensing agencies, hospitals and other certifying organizations and agencies. Links are also provided to features and processes such as the auction/bidding engine 212 and associated service provider qualifier engine 208, bidding fees engine 212 and bids database 210 for enabling users to participate in an interactive on-line healthcare service auctioning process. Links are also provided to other services such as an insurance product transaction engine and associated databases 209 which enable users to obtain various healthcare/professional/licensed service related insurance products and allows insurance underwriters to research historical information for determining prices of their proffered insurance policies.

The HME service also provides multi-level confirmation of a service provider's credentials by linking to other organizations' databases. This process may be performed by transaction system 16 in a manner transparent to the user by Qualifier Engine 208 (service provider authentication engine 71 and qualifier/credentials database 72 in FIG. 1A). For example, the HME system 16 performs a search in an outside Public domain database or subscribed databases using a registrant's name and license number. Confirmations are then displayed for the bidder/user of such services. For example, a provider of proffered healthcare/professional/licensed services lists his/her qualification, board certification and his/her hospital privileges upon registering. Next, in processes that are performed transparently to the on-line user, a qualifier engine 208 will reach out to other commercial and private databases across the Internet to obtain and cross-reference the service provider's identification and credentials information to determine if the qualifications stated/listed by a particular service provider can be verified.

There are multiple types and forms of bidding transactions/processes that are provided by the HME service and web-site. Such may include bids by service providers to provide a particular healthcare service/procedure. Updates to offers and subsequent bids are also processed and posted on-line. Other available transactions may include negotiated bids with counter offers. Alternatively, reserved bidding is also available wherein a provider lists his services with a hidden reserve price below which, until that price is reached, he is not obliged to consume the transaction and there is a Dutch bid in which a number of procedures or hospital beds can be listed at a given price and bidders bid at that price. If all the orders are filled they can voluntarily raise their price to secure a primary position in obtaining such limited services at the specified Dutch bid. In addition, there is a prior transaction database where assessment of similar procedures by similar providers can be traced historically. The HME service also provides a database of the "outcomes" or results of such transactions which may also be supplemented by comments and information obtained, for example, via an on-line user-feedback form web page.

Figure 7A:
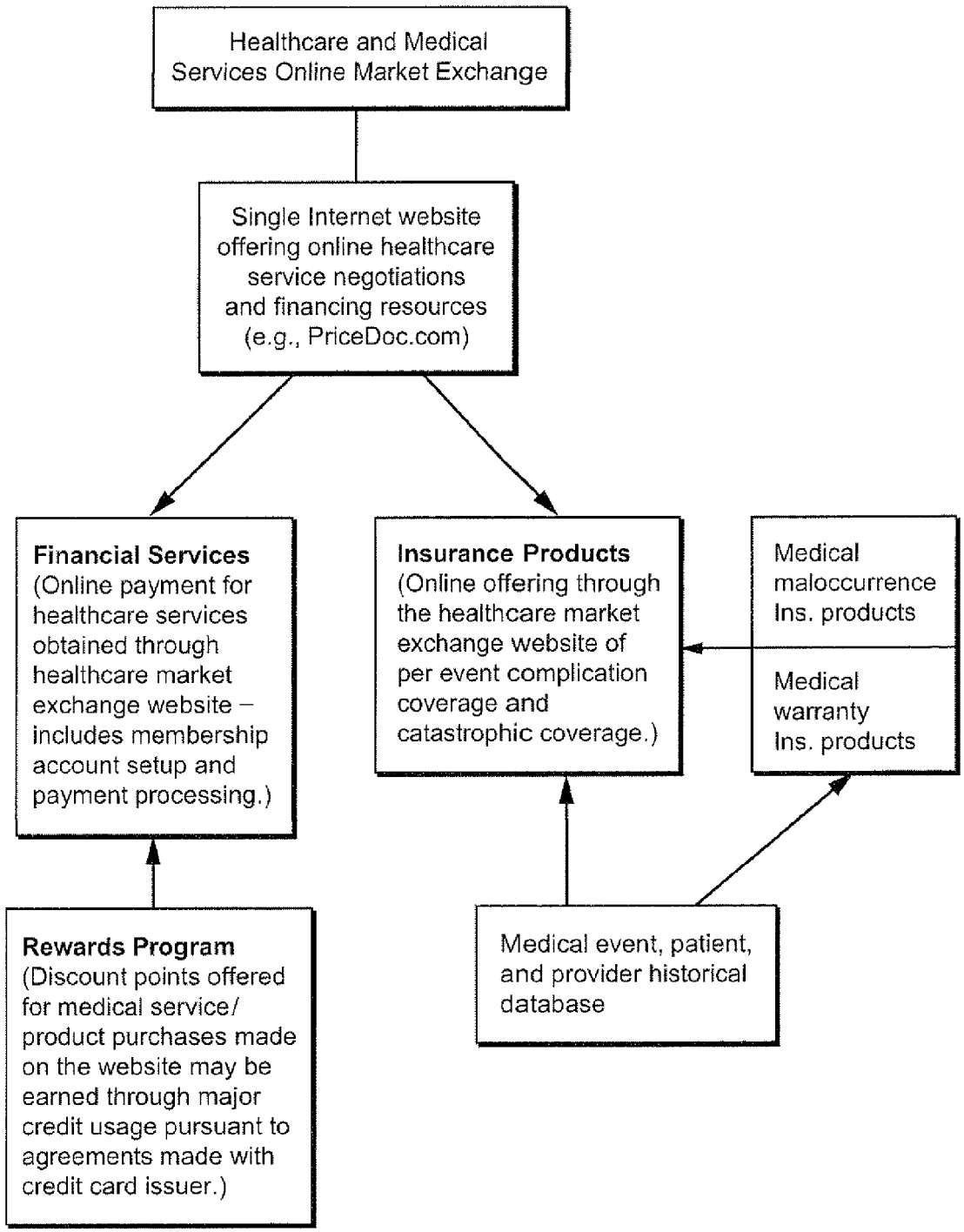
FIG. 7A is a diagram illustrating non-limiting example features and resources provided on-line by the auction transaction and healthcare market exchange system (HME)

FIG. 7A provides an overview of some of the basic features and user resources provided on-line via the on-line auction transaction and healthcare market exchange system (HME) website. The exemplary HME system and web-site business model discussed and disclosed herein is intended to serve as a single comprehensive on-line resource for researching and procuring healthcare services that includes, among other things, an on-line auctioning service for proffering and bidding on proffered healthcare products and services, an on-line resource for participating in negotiations with healthcare service providers concerning the price of proffered products and services, and an on-line service center for procuring and accessing financial resources for funding procured healthcare products and services.

A membership account with the HME is initially set up by a user on-line via the HME web-site. Thereafter, payments for procured healthcare services may be conveniently processed on-line via the HME website. The user may also make on-line arrangements through the web-site to have bids and other healthcare payments financed at least in part through a personal HSA and/or MSA. The use of HSA and MSA accounts to finance bids for services in this manner imparts greater value to a user's personal HSA or MSA account. Moreover, financing bids and other healthcare payments via this pretax HSA pathway further leverages the power of the user's HSA. Databases are automatically accessed by the HME and are employed transparently to the user to determine which particular health care purchases made by a user will qualify for payment via an HSA. The user is then automatically informed as the whether a particular health care product or service qualifies at the time of a negotiated on-line purchase or bid submission. In addition, as a user accumulates unspent funds within his/her personal HSA each year, that user will progressively qualifying for a greater and greater deductible amounts on their catastrophic or other medical insurance coverage and, consequently, will therefore also qualify for lower overall insurance premium payments.

Arrangements may also be made on-line to set up a personal "health-card" through the HME system to automatically debit payments from one or more of the user's accounts including an HSA or MSA. In addition, arrangements may be made on-line with various participating credit card companies to offer rewards, for example, in the form of discount points or cash rebates, for professional/licensed services or products purchased on-line through the HME website when using a particular company's credit card. Likewise, various insurance companies products may also be offered on-line through the HME website such as, for example, per event medical complication coverage and catastrophic medical coverage policies.

Procurement of several medical insurance products is also made available through the HME web-site. For example, one particular unique type of medical insurance product offered by the on-line HME system is a medical/health event-specific warranty coverage that covers the patient for the costs of any unforeseen medical complications which may arise during or as a result of a particular procured healthcare service. Another unique type of medical insurance product offered by the on-line HME system is a no-fault medical maloccurrence insurance product that is analogous to conventional "no-fault" automobile insurance. This no-fault medical mal-occurrence coverage is made available to healthcare/professional/licensed service providers through the HME website and provides monetary compensation to a patient for any medical maloccurrence resulting from treatment for a particular medical/healthcare event. (Of course, the injured patient/claimant always has the option of declining any no-fault compensation so awarded and initiating a lawsuit for malpractice.)

The offering price of such insurance products for a particular patient is be based upon multiple event-related factors such as, for example, historical procedural outcome data compiled for the different professional/licensed service providers, related medical event data for different hospitals, as well as specific information concerning each individual patient's particular condition/complexity. These historical information databases are compiled and maintained by the HME system and selected insurance underwriters are allowed access to this compiled historical medical incident/event information. This enables the provision an event-linked pricing scheme for marketing such insurance products on-line.

For example, in the exemplary on-line healthcare market exchange (HME) system and business method implementation described herein, a "no fault" medical mal-occurrence (i.e., mishap) coverage insurance product is offered and made available on-line to healthcare/professional/licensed service providers that are using the HME service to proffer a particular healthcare/professional/licensed service to prospective on-line patients. This medical "mal-occurrence" insurance is designed to offer healthcare/professional/licensed service providers with at least some degree of protection against unforeseen expenses incurred as a result of a medical mishap or unexpected outcome/result of providing a professional/licensed service/procedure. The cost of this medical "mal-occurrence" insurance coverage is determined, inter alia, by the risks involved in the particular procedure based on one or more factors such as procedural complexity and/or patient complexity, the historical past performance record or procedural "outcomes" (results) for a particular healthcare service provider and the place or hospital where the procedure is performed. Historical data records of such information are collected, stored and maintained by the HME system in databases that are made readily available on-line to qualified insurance underwriters. Such information may also be gathered on-line from prospective patients and healthcare/professional/licensed service providers during the initial HME on-line registration process.

As mentioned above, the HME service also offers and makes available on-line a medical warranty coverage insurance product that is intended to cover any such additional medical care expenses that may result from unanticipated medical expenses encountered during performance of the specific purchased service (i.e., a single medical event/service). This "medical warranty" insurance product is intended to provide insurance coverage for an on-line medical/healthcare service consumer that is linked to a specific medical/healthcare event, a specific patient (personal medical history) and a specific medical/healthcare service provider. The medical warranty coverage insurance can either be purchased separately by the on-line patient/consumer or, alternatively, can be incorporated into the price of a particular purchased professional/licensed service. The price for the medical warranty coverage for a particular person/event/provider medical event is determined in a manner similar to that of the medical mal-occurrence insurance product (i.e., using accumulated historical data concerning past performance of the healthcare provider, the known risks involved in the particular procedure, and other data such as hospital/location where the service is performed). All pertinent medical event-related data is maintained in one or more HME databases and made available on-line to underwriters via the HME system web-site.

The exemplary on-line HME system and business method implementation described herein also provides or makes available on-line a health event-specific insurance product providing coverage for a specific healthcare service. Pricing of this health event-specific insurance product is also determined based on historical data and information collected, stored and maintained in one or more of the HME system databases. Such data is made available to insurance product underwriters and may include, inter alia, accumulated procedural "outcomes" data for a particular healthcare service provider, a particular medical/health event, a particular hospital or specific service, pertinent medical complexity, provider and patient feedback data, location of service, etc. In this manner, by utilizing historical data accumulated by the HME system relating to healthcare service providers, patients, healthcare facilities, medical procedures, etc., a healthcare service insurance product for mal-occurrence, medical warranty and/or specific medical events is offered on-line that has unprecedented accuracy in actuarial pricing and also permits competing insurance product underwriters to use their own proprietary pricing algorithms to formulate competitive offers.

Figure 7B:
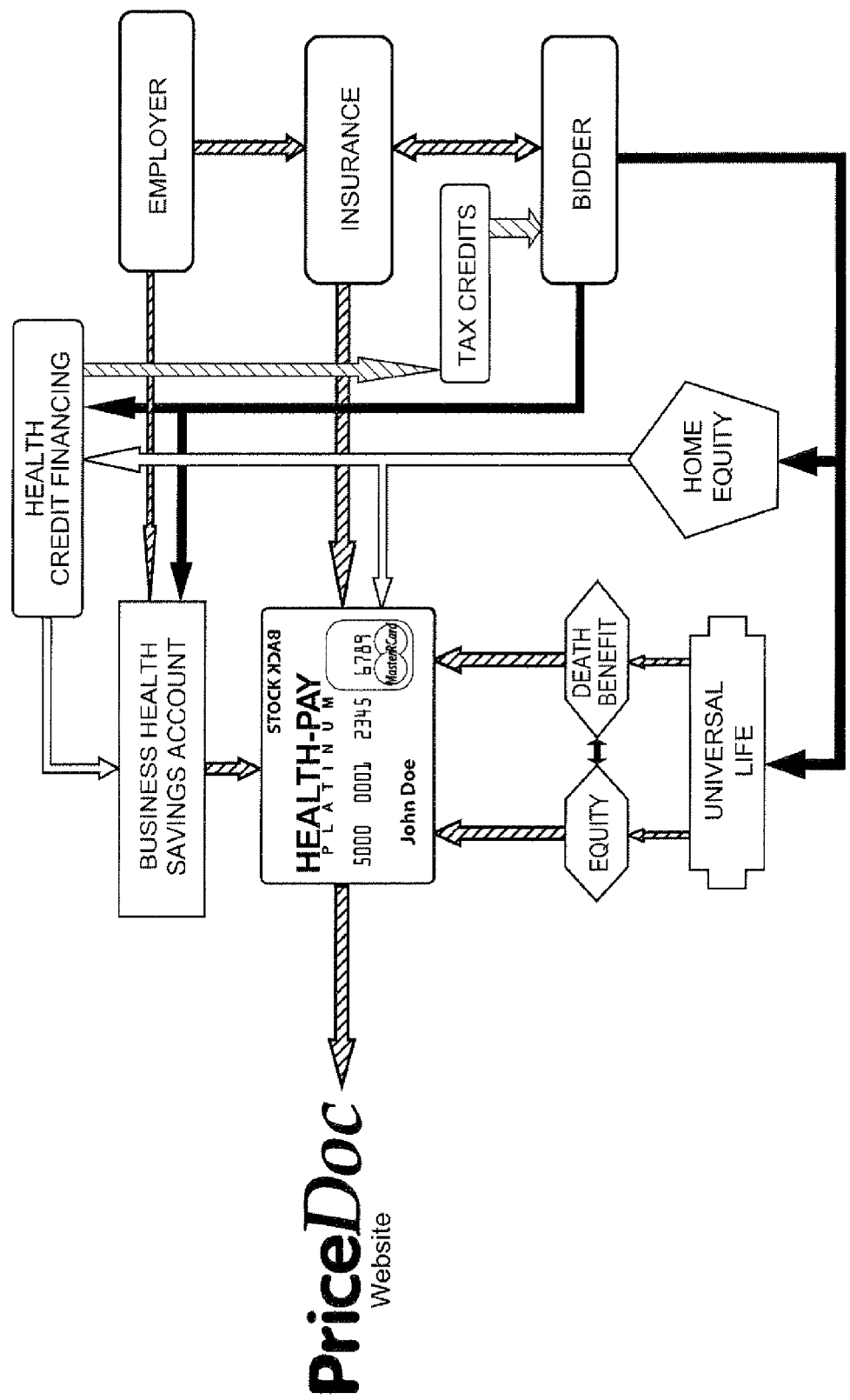
FIG. 7B is a block diagram illustrating some non-limiting example bidder payment options available to a user of the on-line auction transaction and healthcare market exchange system (HME)

A variety of different payment and financing options are made available to a registered members/subscribers of the healthcare market exchange system (HME), as illustrated by the diagram shown in FIG. 7B. For example, payment on a winning bid for the provision of a particular healthcare or professional/licensed service may be financed in part or in whole by using funds from a member user's existing insurance policy, Health. Savings Account (HSA) or an Medical Savings Account (MSA). Arrangements for communicating and directly debiting funds from various commercial and financial sources may be set up through the HME website by a user and automatically carried out in response to one or more on-line initiated instructions by the user. The HME web-site server automatically accesses the appropriate databases in the background to determine which of the user's winning bids or purchases qualify for HSA payment and automatically provides a web-page display informing the user of such at the time of bidding or a negotiated purchase. A very diverse range of sources of funds for financing bids and payments may be set up on-line by a user through the HME system web-site such as, for example, the equity in a life insurance policy or a death benefits insurance policy or the equity in a member user's home. Tax credits for medical expenses may also be recorded and credited automatically to a user's account with the HME.

Alternatively, as previously discussed above, a personal "health-card" payment mechanism similar to a conventional credit card or bank card arrangement may be set up by a user through the HME. The personal user's health-card may be set up through the HME so as to automatically access funds on-line from multiple financial sources and make a variety of payment options available for each and any transaction. A user/bidder may use the health-card to access their HSA and/or MSA to finance bids and make payment for rendered services while on-line through the HME web-site. Financing winning bids for healthcare services via pretax HSA funds further leverages the power of the HSA. In addition, as users accumulate funds in their HSA during the course of a given year, they progress each year toward receiving a higher deductible on any catastrophic medical coverage that they may have and, therefore, will have lower premiums as their HSA builds up.

Figure 8:
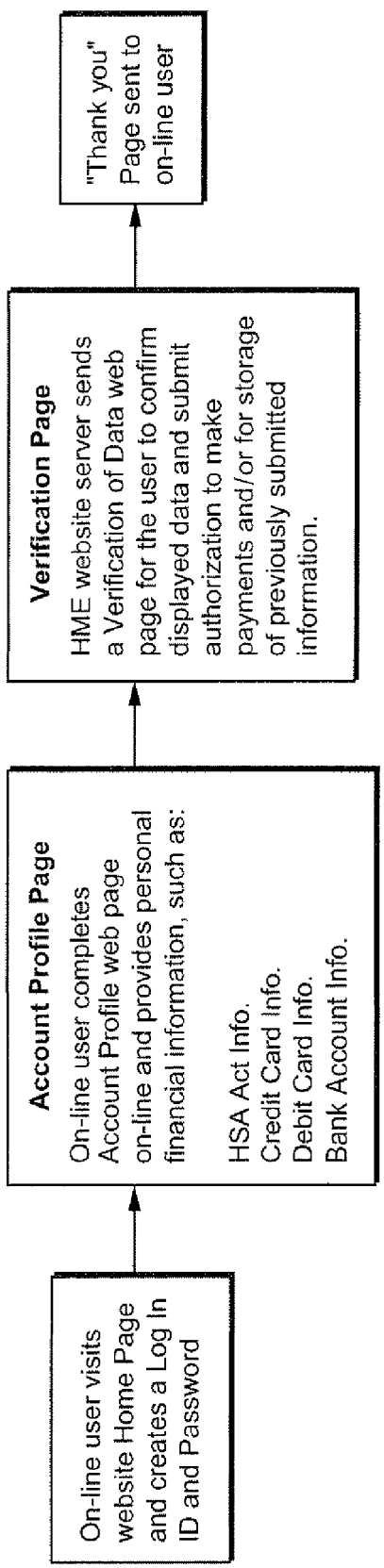
FIG. 8 is a block diagram illustrating a non-limiting example account profile and user sign-up process for an implementation of the on-line auction transaction and healthcare market exchange system (HME)

FIG. 8 illustrates an example account profile and user sign-up process for on-line users/consumers that is implemented by the HME and made accessible on-line via the HME web-site. Upon visiting the HME website home page, a consumer is prompted to create a login ID and a personal password. After creating a login ID and a password, the consumer is prompted to complete an account profile page which provides the system with detailed personal and financial information such as, for example, employer information, personal Health Savings Account information, credit card information, debit card information, information concerning bank accounts, etc. Next, the HME website server provides a Verification Page for sending a verification-of-data notice for the new subscribing user/consumer to accept and submit for storage of the entered personal and financial information and for use by the HME for making payments and conducting transactions.

Figure 9:
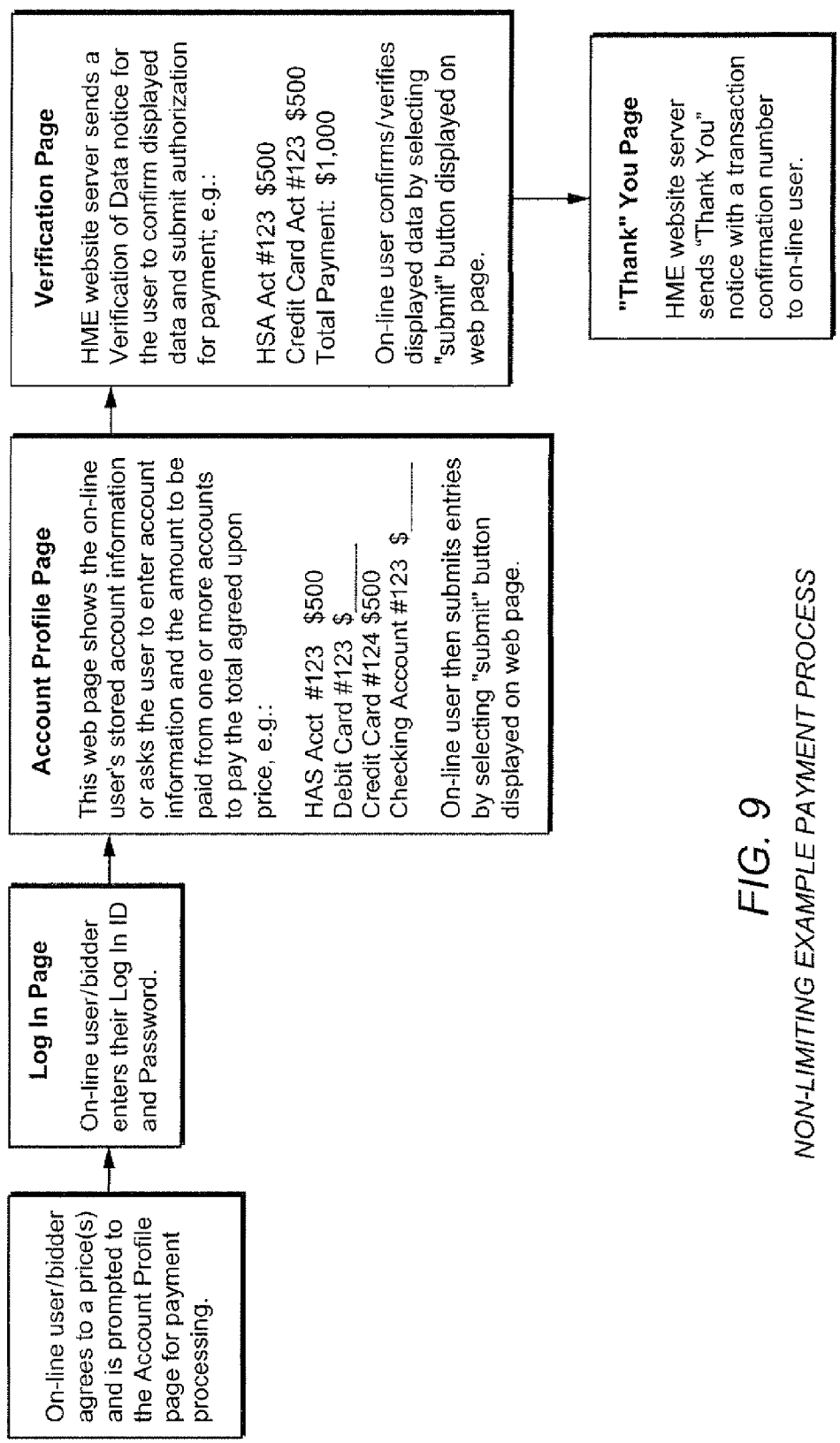
FIG. 9 is a block diagram illustrating a non-limiting example on-line payment process implemented by the on-line auction transaction and healthcare market exchange system (HME)

In FIG. 9, a block diagram is used to illustrate a non-limiting example process implemented by the HME system website that may be used to facilitate on-line payment transactions for winning bids, professional/licensed services and related products. Once an on-line consumer/user agrees to a price for a professional/licensed service or wins a bid for services, the user is prompted to enter their Log-in ID and password, and after verification of the user ID and password, an Account Profile page is presented for payment processing. The Account Profile page shows, for example, the on-line user's stored account information and/or allows the user to enter certain personal account information. The Account Profile page also may show a line-by-line itemization of costs for services and products as well as the total amount or amounts which are to be paid (debited) from one or more sources of funds previously selected or set up by the user for such purposes. After the user submits the requested information, the HME website presents a Verification Page for the user to verify the information submitted and to confirm authorization for the on-line payment. In response, the HME system automatically conducts the appropriate on-line transactions electronically and then provides a 'thank you' or other informational message to the user along with some confirmation of payment such as a transaction number for the user's records.

Figure 10:
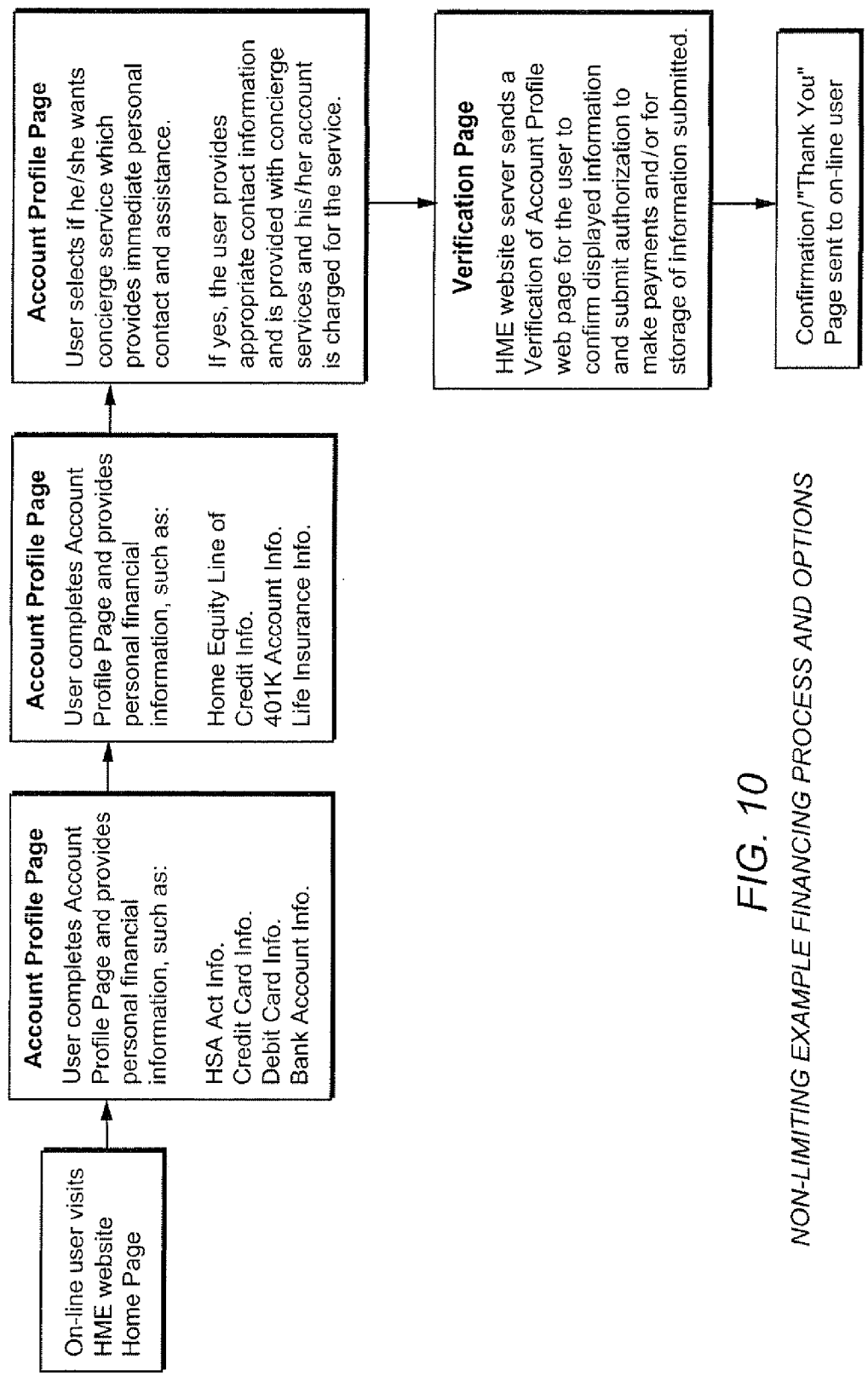
FIG. 10 is a block diagram illustrating a non-limiting example on-line financing process and other user options implemented by the exemplary on-line auction transaction and healthcare market exchange system (HME)

In FIG. 10, a block diagram is used to illustrate a non-limiting example financing process implemented by the HME system as well as some the financing options made available to a user. In this example, upon visiting the HME website homepage, a bidder/customer/user completes an Account Profile page on-line wherein relevant personal financially related information is submitted such as, for example, HSA Act information, personal credit and/or debit card information, bank account information, etc. The HME system may also be set up to provide an optional concierge service arrangement wherein specially trained operators are made immediately available to assist bidders/users/customers. In this case, the user has the option of selecting whether concierge services are to be provided by the HME system and, if so, can submit the appropriate forum and contact information on-line to receive an immediate off-line responsive contact from the concierge operators. The HME website server system then sends a Verification of Account Profile for the user to accept which authorizes the making of payments from the user's accounts.

Figure 11:
FIG. 11 is an image of a non-limiting example home page for an Internet website for the exemplary on-line auction transaction and healthcare market exchange system (HME)
Figure 12:
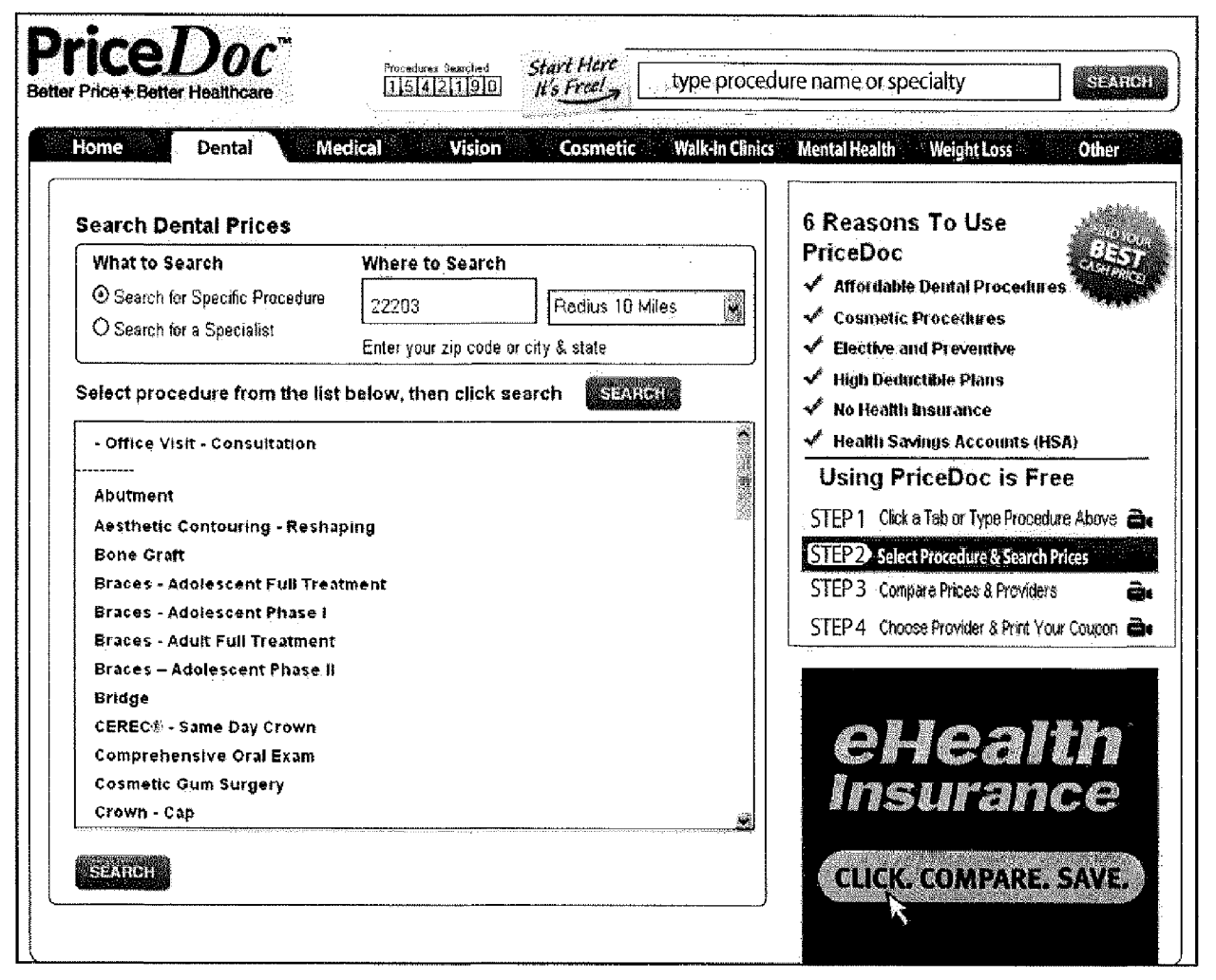
Figure 13:
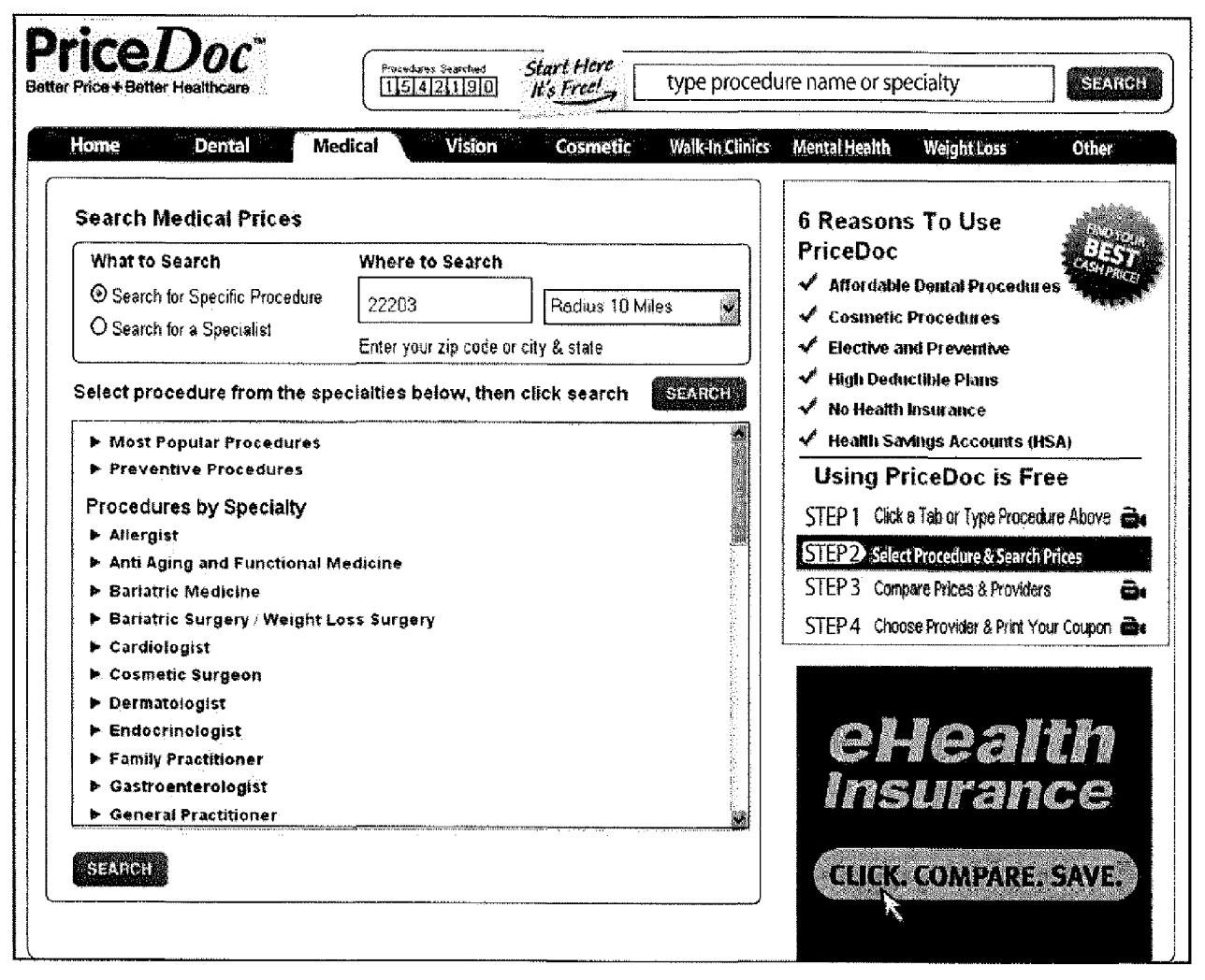
Figure 14:
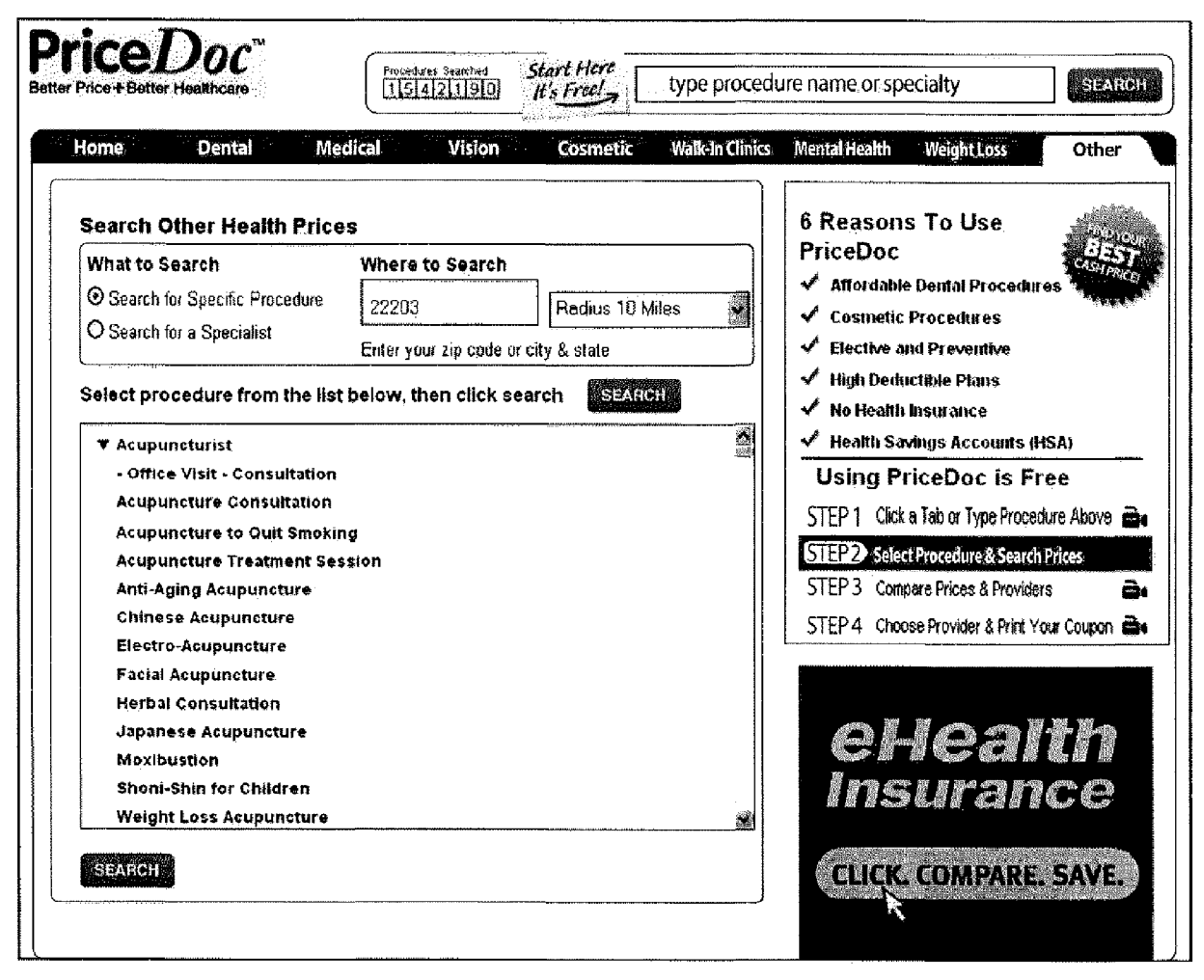
Figure 15:
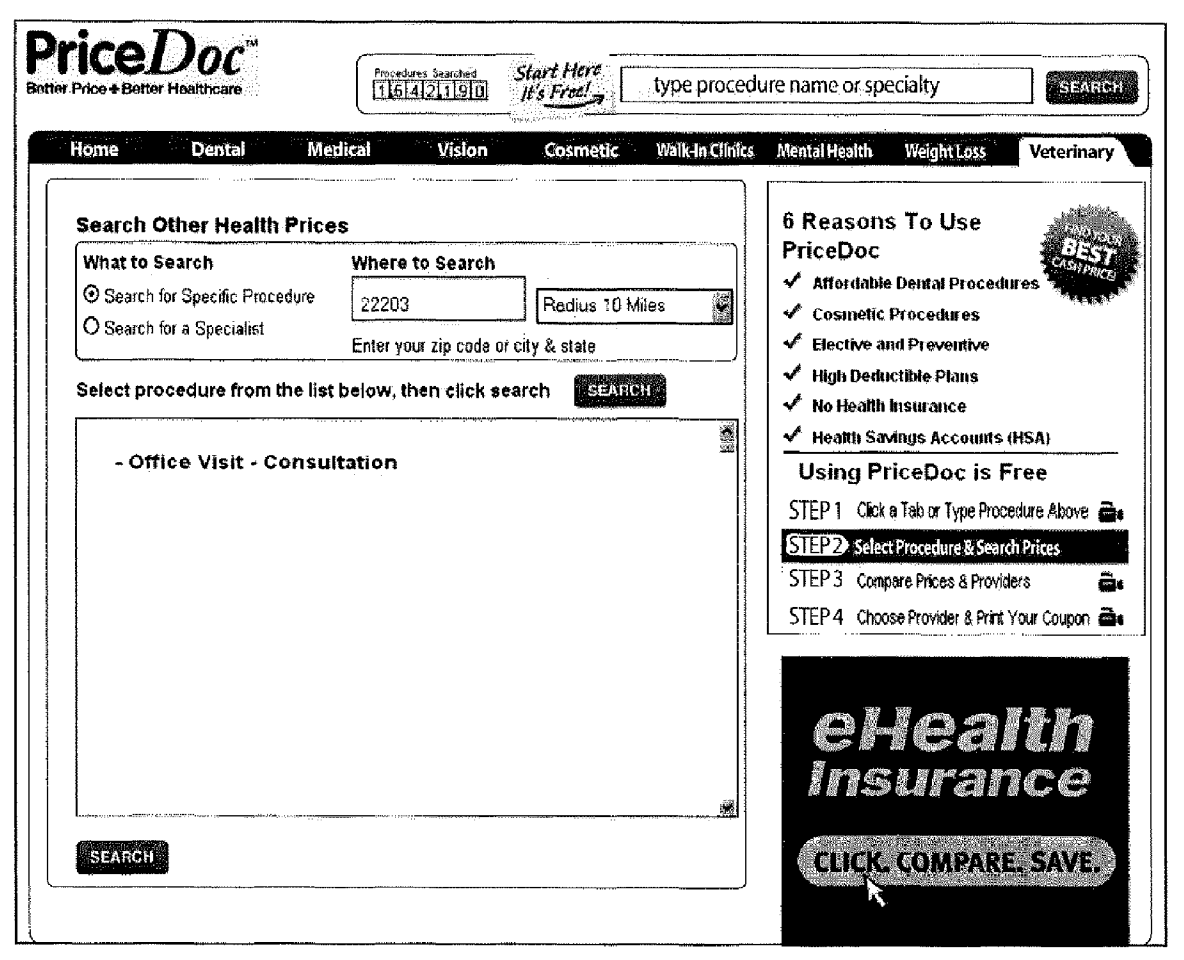

FIGS. 11-15 are some non-limiting examples of Internet web pages for an example Internet website for implementing the on-line auction transaction and healthcare market exchange system (HME) for enabling consumers and service providers to access and use the different aspects and features disclosed herein. For example, FIG. 11 shows an image of a non-limiting example home page for an Internet website for the exemplary on-line auction transaction and healthcare market exchange system (HME). FIG. 12 shows an image of a non-limiting example Internet page for procuring dental services using the exemplary on-line auction transaction and healthcare market exchange system (HME). FIG. 13 shows an image of a non-limiting example Internet page for procuring personal professional/licensed services using the exemplary on-line auction transaction and healthcare market exchange system. (HME). FIG. 14 shows an image of a non-limiting example Internet page for procuring other alternative medical services using the exemplary on-line auction transaction and healthcare market exchange system (HME). FIG. 15 shows an image of a non-limiting example Internet page for procuring Veterinary medical services using the exemplary on-line auction transaction and healthcare market exchange system (HME).

The skilled artisan will appreciate that the apparatus and method of providing an exemplary HME system as disclosed herein may easily be adapted for use in other fields of professional service such as the provision of legal and accounting services, and/or wherever it may be desirable to permit market forces to impact the transactional cost of providing services. While particular exemplary embodiments of the HME on-line transaction system and method have been illustrated and described, it will be obvious to those skilled in the art that various other changes and modifications can be made without departing from the spirit and scope of the invention. The appended claims are therefore intended to cover all such changes and modifications.

What is claimed is:

1. A computer implemented method for providing comparative pricing information and conducting negotiations and/or transactions for services between consumers and licensed/professional service providers of medical, veterinary and/or other healthcare services via the Internet, comprising:

providing a computerized transaction system having one or more web-site servers in communication with the Internet, the servers comprising a pricing and fee negotiations arbitration engine for managing on-line posting and auctioning of medical, healthcare and/or veterinary services/procedures by one or more licensed/professional service providers, the transaction system further comprising one or more databases for storing credentials/accreditations and/or professional licensing information and/or background information of each professional service provider registered to use the transaction system;

using the transaction system to provide an Internet accessible web-site that functions as a medical/healthcare services market exchange for conducting on-line negotiations and/or transactions between one or more prospective patients/consumers and one or more licensed/professional service providers of medical, veterinary and/or other healthcare services over the Internet, wherein the Internet accessible web-site presents on-line offerings and bids for animal medical/healthcare services via said website, and wherein the server automatically researches, verifies and updates the professional licensing information/credentials, of each professional service provider transparently to on-line users and makes that information available to prospective registered bidders online.

2. The method of claim 1 further comprising using the transaction system to provide an on-line user with services that enable conducting on-line research for determining additional information regarding a particular licensed/professional service provider.

3. The method of claim 1 wherein at least some negotiations between one or more on-line prospective patients/consumers and one or more licensed/professional service providers are conducted as a conventional on-line auction process.

4. The method of claim 1 wherein at least some negotiations between one or more on-line users and one or more licensed/professional service providers are conducted as an on-line reverse auction process.

5. The method of claim 1 wherein said databases include information relating to credit worthiness and/or professional credentials of one or more of said on-line users and/or one or more of said licensed/professional service providers.

* * * * *